United States Patent
Chan et al.

(10) Patent No.: US 11,292,803 B2
(45) Date of Patent: Apr. 5, 2022

(54) BIOREDUCIBLE N-OXIDE-BASED PROBES FOR IMAGING OF HYPOXIA

(71) Applicant: THE BOARD OF TRUSTEES OF THE UNIVERSITY OF ILLINOIS, Urbana, IL (US)

(72) Inventors: Jefferson Chan, Savoy, IL (US); Hailey Knox, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 62 days.

(21) Appl. No.: 16/545,990

(22) Filed: Aug. 20, 2019

(65) Prior Publication Data
US 2020/0062784 A1 Feb. 27, 2020

Related U.S. Application Data

(60) Provisional application No. 62/720,530, filed on Aug. 21, 2018.

(51) Int. Cl.
*A61K 51/00* (2006.01)
*A61M 36/14* (2006.01)
*C07F 5/02* (2006.01)
*G01N 21/64* (2006.01)
*A61K 49/00* (2006.01)
*A61K 49/22* (2006.01)

(52) U.S. Cl.
CPC .......... *C07F 5/022* (2013.01); *A61K 49/0021* (2013.01); *A61K 49/22* (2013.01); *G01N 21/6428* (2013.01)

(58) Field of Classification Search
None
See application file for complete search history.

(56) References Cited

U.S. PATENT DOCUMENTS

| | | | |
|---|---|---|---|
| 5,132,327 | A | 7/1992 | Patterson |
| 5,602,278 | A | 2/1997 | Kirkpatrick |
| 6,331,289 | B1 | 12/2001 | Klaveness et al. |
| 7,060,427 | B2 | 6/2006 | Smith et al. |
| 7,576,334 | B2 | 8/2009 | Ashkenazi et al. |
| 2007/0015992 | A1 | 1/2007 | Filkins et al. |
| 2014/0010760 | A1 | 1/2014 | Giri et al. |
| 2014/0213473 | A1 | 7/2014 | Kundu et al. |
| 2016/0113507 | A1 | 4/2016 | Reza et al. |
| 2017/0356884 | A1 | 12/2017 | Hu et al. |

OTHER PUBLICATIONS

Lee et al. (Materials 2013, 6, 1779-1788).*
O'Shea et al. (Chem. Comm. 2006, 1503-1505).*
Hall et al. (J. Org. Chem. 2005, 70, 5571-5578).*
Levi, Jelena, et al., Design, Synthesis, and Imaging of an Activatable Photoacoustic Probe, Journal of American Chemical Society, 132:11264-11269, Jul. 22, 2010.
Li, Hao, et al., Photoacoustic Probes for Ratiometric Imaging of Copper(II), Journal of the American Chemical Society, No. 137:15628-15631 Dec. 11, 2015.
Nishida, Clinton, R., et al., Efficient Hypoxic Activation of the Anticancer Agent AQ4N by CYP2S1 and CYP2W1, Molecular Pharmacology, vol. 78, No. 3, pp. 497-502, Jun. 2010.
Oladipupo, Sunday S. et al., Conditional HIF-1 induction produces multistage neovascularization with stage-specific sensitivity to VEGFR inhibitors and myeloid cell independence, Blood, vol. 117, No. 15, Apr. 14, 2011, 13 pgs.
Wang, Lihong et al., A practical guide to photoacoustic tomography in the life sciences, Nature America, Inc., Nature Methods, vol. 13, No. 8, Aug. 2016, 12 pgs.
Wang, Shichao et al., Activatable photoacoustic and fluorescent probe of nitric oxide for cellular and in vivo imaging, Sensors and Actuators B 267 (Apr. 2018) 403-411.
Knox et al., "Photophysical Tuning of N-Oxide-Based Probes Enables Ratiometric Photoacoustic Imaging of Tumor Hypoxia," ACS Chem Biol., 13(7):1838-1843, Jul. 2018.

* cited by examiner

*Primary Examiner* — Michael G. Hartley
*Assistant Examiner* — Melissa J Perreira
(74) *Attorney, Agent, or Firm* — Haukaas Fortius PLLC; Michael H. Haukaas

(57) ABSTRACT

Hypoxia occurs when limited oxygen supply impairs physiological functions and is a pathological hallmark of many diseases including cancer and ischemia. Thus, detection of hypoxia can guide treatment planning and serve as a predictor of patient prognosis. Current methods suffer from invasiveness, poor resolution and low specificity. To address these limitations, various hypoxia-responsive probes (HyPs) for photoacoustic imaging are disclosed. The emerging modality converts safe, non-ionizing light to ultrasound waves, enabling acquisition of high-resolution 3D images in deep tissue. The HyPs feature an N-oxide trigger that is reduced in the absence of oxygen by haem proteins such as CYP450 enzymes. Reduction of HyPs produce a spectrally distinct product, facilitating identification via photoacoustic imaging. HyPs exhibit selectivity for hypoxic activation in vitro, in living cells and in multiple disease models in vivo. HyPs are also compatible with NIR fluorescence imaging, establishing its versatility as a multimodal imaging agent.

17 Claims, 15 Drawing Sheets a 2-Nitroimidazole design strategy b This work

HyP-1
$\lambda_{nm} = 672$ nm red-HyP-1
$\lambda_{nm} = 760$ nm

BIOREDUCIBLE N-OXIDE-BASED PROBES FOR IMAGING OF HYPOXIA

RELATED APPLICATIONS

This application claims priority under 35 U.S.C. § 119(e) to U.S. Provisional Patent Application No. 62/720,530, filed Aug. 21, 2018, which is incorporated herein by reference.

BACKGROUND OF THE INVENTION

Hypoxia occurs when tissue oxygen supply is restricted, leading to significant changes in oxygen-dependent physiological processes. The importance of proper oxygen regulation is evident from the variety of disease states associated with hypoxia, such as coronary and peripheral artery diseases, alcoholic liver injury and gastrointestinal inflammatory conditions. Additionally, an estimated 50-60% of solid tumours contain hypoxic regions, which is noteworthy considering that hypoxic tumours are commonly associated with treatment resistance, aggressive phenotypes and high metastatic potential. Approximately 90% of breast cancer deaths occur as the result of metastasis, which is strongly promoted by increased intratumoural levels of hypoxia-inducible factors. Rapid and specific hypoxia detection in vivo is therefore of great significance in both preclinical and clinical settings. Specifically, the ability to reliably and non-invasively detect hypoxia in real time can provide critical information to predict treatment responses and enable patient-specific treatment plans.

The current gold standard of hypoxia detection is the oxygen-sensitive electrode, which is inserted into the tissue of interest to provide a direct measure of oxygen partial pressure. Although this technique enables oxygen detection with high sensitivity and accuracy, it is extremely invasive and therefore only applicable when tissue is accessible, such as in superficial tumours of the head and neck. As such, significant effort has been put forth to develop alternative methods for non-invasive hypoxia detection. Optical imaging with hypoxia-responsive fluorescent probes has enabled visualization of hypoxia in living cells with excellent subcellular resolution. However, due to high scattering and limited penetration of light in biological tissue, fluorescent probes suffer greatly from poor resolution beyond an imaging depth of 1 mm. Likewise, positron emission tomography (PET)-based hypoxia detection using various $^{18}$F-labeled radiotracers also faces major obstacles including high background due to non-specific uptake and limited spatial resolution. Together, these drawbacks hamper the ability to confidently discern specific hypoxic regions using PET imaging.

Photoacoustic (PA) imaging is a rapidly emerging modality that utilizes near-infrared (NIR) light from a pulsed laser source to induce temperature and pressure fluctuations in tissue, producing ultrasound waves that can be detected using acoustic transducers. Because the scattering of sound in biological tissues is three orders of magnitude less than the scattering of light, these signals can be reconstructed to produce high-resolution 3D images (e.g., tens of microns) in deep tissue (e.g., cm range). In addition to superior resolution at these depths, PA imaging is a safer alternative compared to other techniques owing to the use of non-ionizing light. This property enables longitudinal tracking of disease progression without the risk of overexposure to harmful radiation. Despite these advantages, there are currently no NIR-absorbing small-molecule PA imaging agents that allow for detection of specific tissue microenvironments via signal enhancement, although several peptide and nanoparticle-based designs have been reported.

Accordingly, there is a need for a multimodal NIR-absorbing small-molecule imaging agents that allow for detection of specific tissue microenvironments via signal enhancement.

SUMMARY

In this disclosure the development of various hypoxia-responsive probes (HyPs), such as Hypoxia Probe 1 (HyP-1), for PA imaging, is presented. HyPs features an N-oxide-based trigger that can undergo facile bioreduction in the absence of oxygen.

Accordingly, this disclosure provides a compound comprising:
  a) a bidentate structure having two or more aromatic conjugated groups and two binding heteroatoms;
  b) a bridging moiety bonded to the binding heteroatoms of the bidentate structure;
  c) an optional electron donating substituent conjugated to one group of the two or more conjugated groups; and
  d) a redox moiety conjugated to a second group of the two or more conjugated groups;
wherein the redox moiety is a substrate for redox reactions; and
wherein the compound absorbs electromagnetic radiation at about the near infrared (NIR) region of the electromagnetic spectrum.

In various embodiments, the compound is a compound of Formula I:

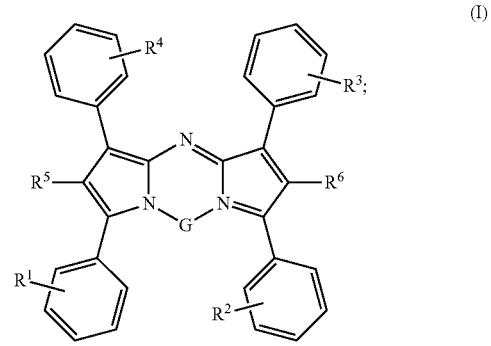

wherein
  G comprises a metalloid;
  $R^1$ is a redox moiety;
  $R^2$ is an electron donating substituent;
  $R^3$, $R^4$, $R^5$ and $R^6$ are independently H, halo, —($C_1$-$C_6$)alkyl, —($C_3$-$C_6$)cycloalkyl, —$OR^a$, —$SR^b$, or —N(J)($R^c$)$_2$ wherein J is a lone pair or O$^-$;
  each $R^a$ and $R^b$ are independently H, —($C_1$-$C_6$)alkyl, or —($C_3$-$C_6$)cycloalkyl; and
  each $R^c$ is independently H, —($C_1$-$C_6$)alkyl, or —($C_3$-$C_6$)cycloalkyl.

This disclosure also provides a method for fluorescence detection of hypoxia comprising:
  a) contacting cells and the compound disclosed above wherein the compound is an oxidized compound having an oxidized redox moiety, wherein the oxidized compound and test cells form a test sample;
  b) contacting control cells with the oxidized compound, wherein the oxidized compound and the control cells form a control sample;

c) allowing an interval of time to elapse wherein the oxidized redox moiety of the oxidized compound is irreversibly reduced by endogenous reducing agents to form a reduced compound in the test sample when the test cells are deprived of oxygen;

d) irradiating the test sample and control sample with NIR radiation causing the test sample and control sample to emit a fluorescent signal;

e) determining the ratiometric intensity of the fluorescent signal of the test sample and control sample; and f) detecting the presence of hypoxia in the test sample when the fluorescent signal of the test sample has an intensity greater than the fluorescent signal of the control sample; or detecting the absence of hypoxia in the test sample when the fluorescent signal of the test sample has an intensity about the same as the fluorescent signal of the control sample; wherein the fluorescent signal of the reduced compound is red shifted by a wavelength of about 50 nm to about 200 nm relative to the compound of claim 12 when hypoxia is present.

Additionally, this disclosure provides a method for photoacoustic detection of hypoxia comprising:

a) contacting tissue and the compound disclosed above in-vivo, wherein the compound is an oxidized compound having an oxidized redox moiety, wherein the oxidized compound and tissue form a sample;

b) allowing an interval of time to elapse wherein the oxidized redox moiety of the oxidized compound is irreversibly reduced by endogenous reducing agents to form a reduced compound in the test sample when the tissue is deprived of oxygen;

c) irradiating the sample with NIR radiation; and d) detecting a photoacoustic signal from the sample wherein the reduced compound emits a photoacoustic signal;

thereby detecting the presence of hypoxia when present in the sample.

thereby the presence of hypoxia when present in the sample is detected.

Furthermore, the invention provides novel compounds of Formula I and Formula II, intermediates for the synthesis of compounds of Formula I and Formula II, as well as methods of preparing compounds of Formula I and II. The invention also provides compounds of Formula I and II that are useful as intermediates for the synthesis of other useful compounds. The invention provides for the use of compounds of Formula I and Formula II for the manufacture of imaging agent useful for the detection of hypoxia in cells or a subject, such as a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
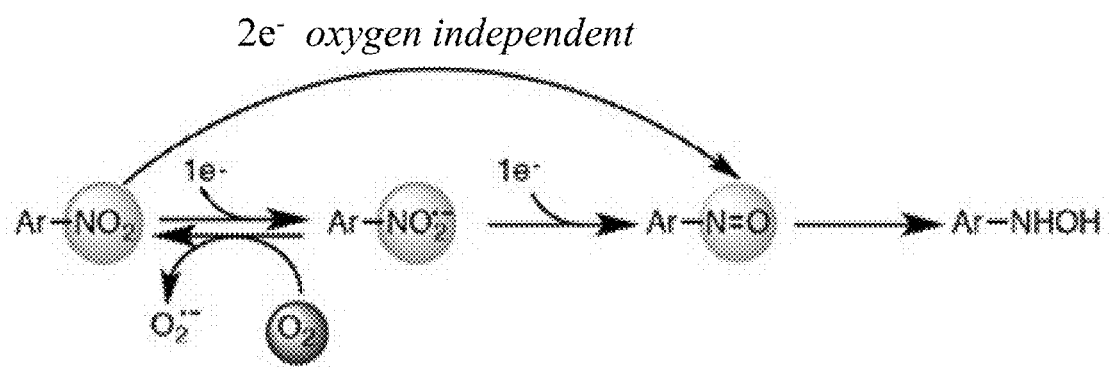
FIG. 1. Design strategies used for hypoxia-responsive probe development. (a) Enzymatic reduction of 2-nitroimadazoles. One-electron reductases reduce the nitro to the corresponding nitro radical anion, which can be rapidly reversed by oxygen. In the absence of oxygen, a subsequent reduction affords the nitroso, which can then undergo further reduction and irreversible crosslinking with intracellular nucleophiles. (b) Chemical structure of HyP-1 and red-HyP-1. HyP-1 undergoes irreversible two-electron reduction by haem proteins such as CYP450 enzymes in the absence of oxygen, which binds competitively to the haem iron. Red-HyP-1 produces an enhanced PA signal (rings) upon irradiation at 770 nm (wavy arrow).
Figure 1:
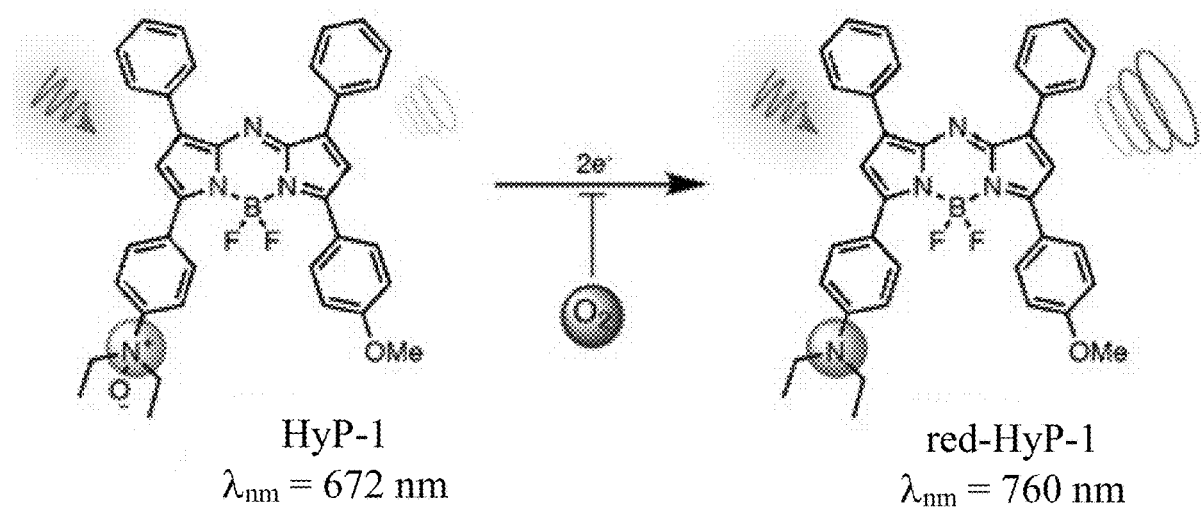

Current hypoxia-specific molecular sensors often employ the 2-nitroimdazole moiety as a hypoxia-responsive trigger. This strategy is based on hypoxia-selective reduction of the nitro functional group ($—NO_2$) to various reactive intermediates by various one-electron reductases. However, the major drawback of this system is that only one electron reduction of the nitro group is oxygen dependent. The nitro group can be reduced by certain enzyme classes in an oxygen-independent manner, resulting in unwanted background signal. Additionally, nitro groups can be reduced by bacterial nitroreductases in an oxygen-independent manner, providing another source of false positive signal. Hypoxia detection with 2-nitroimidazoles is also most commonly associated with chronic hypoxia, while an ideal strategy would enable rapid detection of both chronic and acute hypoxia. The N-oxide functional group therefore provides an alternative strategy that may enable rapid and selective hypoxia detection with minimal background. N-oxides have been previously used for hypoxia-specific activation of cancer prodrugs which supports the feasibility of the disclosed approach.

The design of the disclosed imaging agents was inspired by AQ4N, a hypoxia-responsive cancer prodrug containing two N-oxide moieties that mask its cytotoxic effects prior to reduction in hypoxic tissue. Although N-oxides have been employed for fluorescence sensing of Fe(II), bioorthogonal conjugation reactions and flow cytometric analysis of apoptotic cell populations; this functionality has not previously been demonstrated for specific hypoxia detection. The PA response of HyP-1 relies on the ability of the N-oxide to modulate its optical properties. Specifically, conversion of the N-oxide to the corresponding aniline (red-HyP-1) elicits a bathochromic (red) shift in the absorbance from 670 to 760 nm. Because HyP-1 does not absorb at this wavelength, the PA signal produced upon excitation at 760 nm corresponds exclusively to red-HyP-1. Therefore, hypoxia detection is made possible by determining the signal enhancement observed at this wavelength. Additionally, because both HyP-1 and red-HyP-1 are fluorescent, HyP-1 can be employed for ratiometric NIR fluorescence imaging in both living cells and animal models. Rapid and selective hypoxia-mediated activation of HyP-1 is observed both in vitro and in cancer cells cultured under hypoxic conditions. HyP-1 can be applied to hypoxia detection in vivo, which is demonstrated with the application of a hypoxic tumor model. Importantly, HyP-1 is unlike many cancer-specific hypoxia imaging probes that rely on enzyme upregulation for activation to occur. In addition to intratumoural hypoxia, HyP-1 can also reliably detect oxygen deficiencies in vivo in a hindlimb ischemia model of peripheral artery disease (PAD). The success of HyP-1 in these different disease models is indicative of its versatile capabilities and applicability to hypoxia detection.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N (R')$_2$, SO$_3$R', C(O)R', C(O)C(O)R', C(O)CH$_2$C(O)R', C(S) R', C(O)OR', OC(O)R', C(O)N(R')$_2$, OC(O)N(R')$_2$, C(S)N (R')$_2$, (CH$_2$)$_{0-2}$NHC(O)R', N(R')N(R')C(O)R', N(R')N(R')C (O)OR', N(R')N(R')CON(R')$_2$, N(R')SO$_2$R', N(R') SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR') R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, 3-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "conjugated" or "conjugation" are terms understood by ordinary person skilled in the art. The terms refer to a system of connected p-orbitals with delocalized electrons in a molecule, which in general lowers the overall energy of the molecule and increases stability. It is conventionally represented as having alternating single and multiple bonds. Lone pairs, radicals or carbenium ions may be part of the system, which may be cyclic, acyclic, linear or mixed. Conjugation is the overlap of one p orbital with another across an intervening a bond. Electron donating or withdrawing groups can increase or decrease the electron density of the conjugated system by resonance.

The term "electron donating (EDG)" or "electron releasing (ERG)" are terms understood by ordinary person skilled in the art. The terms refer to a group or substituent that releases electrons into a molecule which group can modify electrostatic forces operating on a reaction center, for example, to cause a chemical reaction. The EDG can also stabilize an electron deficient moiety in said molecule. Examples of EDGs include, but are not limited to alkyl groups, alkoxy groups, amino groups. Even halo can be an EDG via resonance (conjugation) of the halo's lone pair. On the other hand, an electron withdrawing group (EWG) would, for example, draw electrons away from a reaction center.

The term "electron deficient" is a term understood by ordinary person skilled in the art that describes atoms or molecules having fewer than the number of electrons required for maximum stability. At the atomic level, main group atoms having less than 8 electrons or transition metal atoms having less than 18 electrons are described as electron deficient. For example, boron and can be electron-deficient when it lacks an octet of electrons around the central boron atom. This deficiency accounts for boron being a strong Lewis acid.

The term "metalloid" refers to a type of chemical element which has properties in between, or that are a mixture of, those of metals and nonmetals. The metalloids are the elements found along the step like line between metals and non-metals of the periodic table. The metalloids are boron (B), aluminum (Al), silicon (Si), germanium (Ge), arsenic (As), selenium (Se), antimony (Sb), tellurium (Te), polonium (Po) and astatine (At).

The term "near infrared (NIR)" refers to a region of the electromagnetic spectrum from 780 nm to 2500 nm. When the term is modified by the term "about" (discussed above) then the range can be 780 nm±25% to 2500 nm±25%. Typical applications include but are not limited to medical and physiological diagnostics and imaging.

Embodiments of the Invention

This disclosure provides a compound comprising:
a) a bidentate structure having two or more aromatic conjugated groups and two binding heteroatoms;
b) a bridging moiety bonded to the binding heteroatoms of the bidentate structure;
c) an optional electron donating substituent conjugated to one group of the two or more conjugated groups; and
d) a redox moiety conjugated to a second group of the two or more conjugated groups;
wherein the redox moiety is a substrate for redox reactions; and
wherein the compound absorbs electromagnetic radiation at about the near infrared (NIR) region of the electromagnetic spectrum.

In various embodiments, the compound comprises the electron donating substituent and the compound is unsymmetrical, wherein the electron donating substituent and redox moiety are different moieties (e.g., do not have the same functionality, for example, said substituent and moiety have different functional groups, such as a methoxy and diethylamino substituents).

In various embodiments the bidentate structure has a core structural moiety having an axis of symmetry that is $C_2$-symmetric. In other various embodiments the electron donating substituent is an alkoxy substituent.

In some embodiments, the compound is asymmetrical. In some embodiments, the compound is symmetrical. In some embodiments, the compound is asymmetrical and the redox moiety is in oxidized form. In some embodiments, the compound is asymmetrical and the redox moiety is in reduced form. In some embodiments, the compound is symmetrical and the redox moiety is in oxidized form. In some embodiments, the compound is symmetrical and the redox moiety is in reduced form.

In additional embodiments, the redox moiety comprises nitrogen. In other embodiments, the redox moiety comprises an alkylamine. In further embodiments, the redox moiety comprises an N-oxide. In further embodiments, the bridging moiety comprises an electron deficient atom. In yet other embodiments, the bridging moiety comprises boron. In other various embodiments the bidentate structure comprises a tetraarylazadipyrromethene.

In some embodiments, the compound comprises a bidentate structure having two or more conjugated groups. In some other embodiments, the compound comprises a bidentate structure having two or more conjugated groups and two binding heteroatoms. In further embodiments, the compound comprises a bidentate structure having two or more phenyl conjugated groups (and two binding heteroatoms). In other embodiments, the aromatic or phenyl conjugated groups are substituted (optionally) with any of the substituents described above in this disclosure. In additional embodiments, the compound comprises 2, 3, or 4 conjugated groups.

In various additional embodiments, the compound absorbs electromagnetic radiation at a wavelength of about 600 nm to about 1000 nm, about 500 nm to about 2000 nm, about 600 nm to about 800 nm, about 650 nm to about 850 nm, or about 625 nm to about 825 nm. In various additional embodiments, the compound exhibits a Stokes shift (e.g., in the fluorescence absorption and emission spectra) of about 25 nm to about 250 nm, about 75 nm to about 150 nm, about 85 nm to about 125 nm, or about 80 nm to about 100 nm. In other various embodiments, the compound has an extinction coefficient of about $0.01 \times 10^4$ to about $100 \times 10^4$ or any range of values in between. In further various embodiments, the compound has a quantum yield of about 0.01 to about 0.9 or any range of values in between.

In further embodiments, the redox moiety is a reduced redox moiety (e.g., a dialkylamine) of a reduced compound (e.g., Red-HyP-1), and the reduced compound is fluorescent when irradiated at NIR wherein fluorescence of the reduced compound is red shifted by about 50 nm to about 200 nm relative to a corresponding oxidized compound (e.g., HyP-1) having an oxidized redox moiety (e.g., an N-oxide of the dialkylamine). In other embodiments, said red shift is about 25 nm to about 250 nm, about 75 nm to about 150 nm, about 85 nm to about 125 nm, or about 80 nm to about 100 nm.

In other additional embodiments, the reduced compound emits a photoacoustic signal when irradiated at NIR. In yet other various embodiments, the compound is a compound of Formula I:

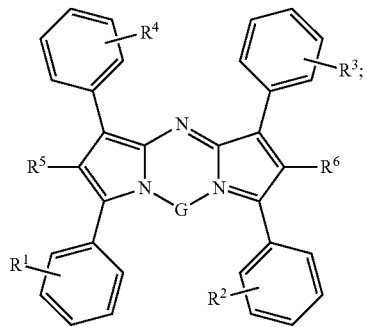

(I)

wherein

G comprises a metalloid or metal;

$R^1$ is a redox moiety;

$R^2$ is H or an electron donating substituent;

$R^3$, $R^4$, $R^5$ and $R^6$ are independently H, halo, —($C_1$-$C_6$) alkyl, —($C_3$-$C_6$)cycloalkyl, —$OR^a$, —$SR^b$, or —N(J)($R^c$)$_2$ wherein J is a lone pair or $O^-$;

each $R^a$ and $R^b$ are independently H, —($C_1$-$C_6$)alkyl, or —($C_3$-$C_6$)cycloalkyl; and each $R^c$ is independently H, —($C_1$-$C_6$)alkyl, or —($C_3$-$C_6$)cycloalkyl.

In some embodiments, G is $BX_2$; and X is halo. In other embodiments, X is fluoro, chloro, bromo, or iodo.

In some other embodiments of the above compound, $R^1$ is —N(L)($R^d$)$_2$;

L is a lone pair or O; and each $R^d$ is independently H, —($C_1$-$C_6$)alkyl, or —($C_3$-$C_6$)cycloalkyl, or both $R^d$ taken together form a heterocycle with the nitrogen atom of $R^1$.

In yet other embodiments, $R^2$ is H, halo, —($C_1$-$C_6$)alkyl, —($C_3$-$C_6$)cycloalkyl, —$OR^a$, —$SR^b$, or —N(Z)($R^e$)$_2$ wherein Z is a lone pair or $O^-$; and each $R^e$ is independently H, —($C_1$-$C_6$)alkyl, or —($C_3$-$C_6$)cycloalkyl, or both $R^e$ taken together form a heterocycle when $R^2$ is —N(Z)($R^e$)$_2$.

In some other embodiments, the compound of Formula I is a compound of Formula II:

(II)

wherein

X is halo;

$R^2$ is H, halo, —($C_1$-$C_6$)alkyl, —($C_3$-$C_6$)cycloalkyl, —$OR^a$, —$SR^b$, or —N(Z)($R^e$)$_2$;

L and Z are a lone pair or $O^-$;

$R^a$ and $R^b$ are independently —($C_1$-$C_6$)alkyl or —($C_3$-$C_6$) cycloalkyl;

each $R^d$ is independently —($C_1$-$C_6$)alkyl or —($C_3$-$C_6$) cycloalkyl, or both $R^d$ taken together form a heterocycle with the nitrogen atom; and each $R^e$ is independently —($C_1$-$C_6$)alkyl, or —($C_3$-$C_6$) cycloalkyl, or both $R^e$ taken together form a heterocycle when $R^2$ is —N(Z)($R^e$)$_2$.

In additional embodiments, the compound of Formula I is a compound of Formula II:
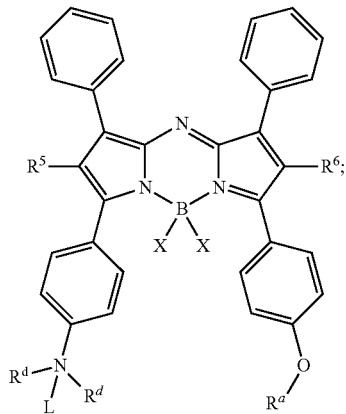
(IIB)
wherein
  X is halo;
  L is a lone pair or O;
  $R^a$ is —$(C_1$-$C_6)$alkyl or —$(C_3$-$C_6)$cycloalkyl; and
  each $R^d$ is independently —$(C_1$-$C_6)$alkyl or —$(C_3$-$C_6)$cycloalkyl.
In further embodiments, the compound of Formula II is HyP-1, Red-HyP-1, rHyP-1, Red-rHyP-1, HyP-650, or Red-HyP-650:
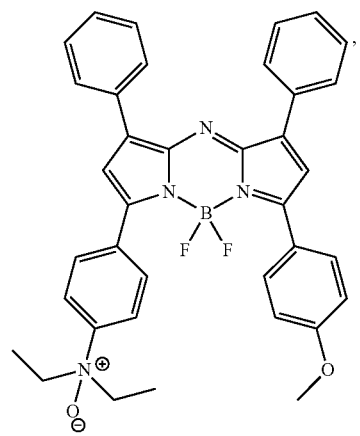
(HyP-1)
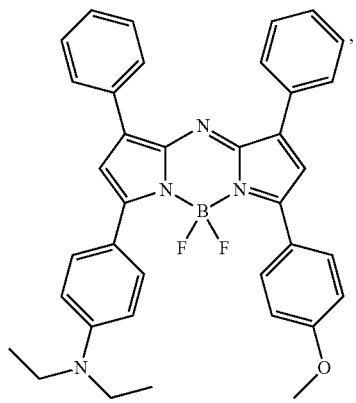
(Red-HyP-1)
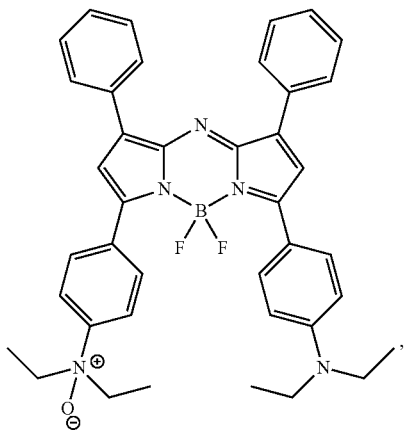
(rHyP-1)
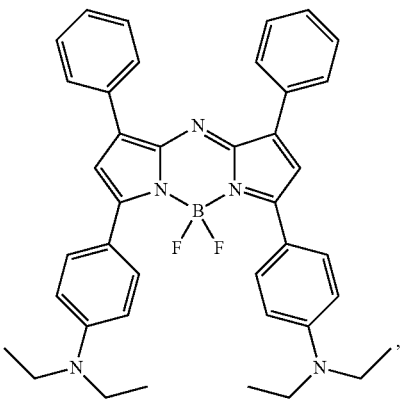
(Red-rHyP-1)
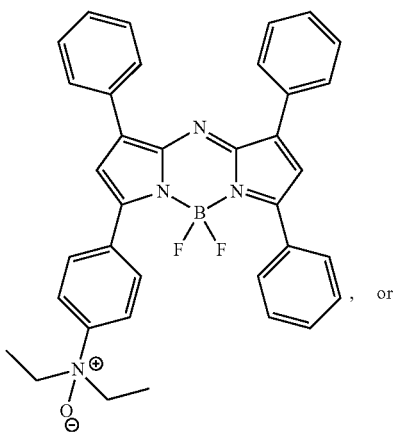
(HyP-650), or -continued

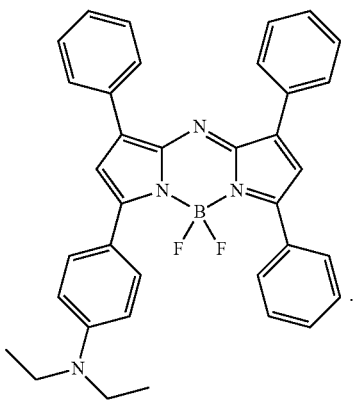

(Red-HyP-650)

In some embodiments, the compound is 4-(5,5-difluoro-7-(4-methoxyphenyl)-1,9-diphenyl-5H-5$\lambda^4$,6$\lambda^4$-dipyrrolo[1,2-c:2',1'-f][1,3,5,2]triazaborinin-3-yl)-N,N-diethylaniline oxide. In other embodiments, the compound is 4-(5,5-difluoro-7-(4-methoxyphenyl)-1,9-diphenyl-5H-5$\lambda^4$,6$\lambda^4$-dipyrrolo[1,2-c:2',1'-f][1,3,5,2]triazaborinin-3-yl)-N,N-diethylaniline. In other embodiments, the compound is 4-(7-(4-(diethylamino)phenyl)-5,5-difluoro-1,9-diphenyl-5H-5$\lambda^4$,6$\lambda^4$-dipyrrolo[1,2-c:2',1'-f][1,3,5,2]triazaborinin-3-yl)-N,N-diethylaniline oxide. In yet other embodiments, the compound is 4,4'-(5,5-difluoro-1,9-diphenyl-5H-4$\lambda^4$,5$\lambda^4$-dipyrrolo[1,2-c:2',1'-f][1,3,5,2]triazaborinine-3,7-diyl)bis(N,N-diethylaniline). In other embodiments, the compound is 4-(5,5-difluoro-1,7,9-triphenyl-5H-5$\lambda^4$,6$\lambda^4$-dipyrrolo[1,2-c:2',1'-f][1,3,5,2]triazaborinin-3-yl)-N,N-diethylaniline. In further embodiments, the compound is 4-(5,5-difluoro-1,7,9-triphenyl-5H-5$\lambda^4$,6$\lambda^4$-dipyrrolo[1,2-c:2',1'-f][1,3,5,2]triazaborinin-3-yl)-N,N-diethylaniline oxide.

In various embodiments, the molecular weight of the composed disclosed herein is about 400 atomic mass units (amu) to about 800 amu, about 450 amu to about 750 amu, about 500 amu to about 700 amu, about 550 amu, to about 675 amu, or about 560 amu to about 660 amu.

This disclosure also provides a method for fluorescence detection of hypoxia comprising:
a) contacting cells and the compound disclosed above, wherein the compound is an oxidized compound having an oxidized redox moiety, wherein the oxidized compound and test cells form a test sample;
b) contacting control cells with the oxidized compound, wherein the oxidized compound and the control cells form a control sample;
c) allowing an interval of time to elapse wherein the oxidized redox moiety of the oxidized compound is irreversibly reduced by endogenous reducing agents to form a reduced compound in the test sample when the test cells are deprived of oxygen;
d) irradiating the test sample and control sample with NIR radiation causing the test sample and control sample to emit a fluorescent signal;
e) determining the ratiometric intensity of the fluorescent signal of the test sample and control sample; and
f) detecting the presence of hypoxia in the test sample when the fluorescent signal of the test sample has an intensity greater than the fluorescent signal of the control sample; or
detecting the absence of hypoxia in the test sample when the fluorescent signal of the test sample has an intensity about the same as the fluorescent signal of the control sample;

wherein the fluorescent signal of the reduced compound is red shifted by a wavelength of about 50 nm to about 200 nm relative to the compound of claim 12 when hypoxia is present.

Additionally, this disclosure provides a method for photoacoustic detection of hypoxia comprising:
a) contacting tissue and the compound disclosed above in-vivo, wherein the compound is an oxidized compound having an oxidized redox moiety, wherein the oxidized compound and tissue form a sample;
b) allowing an interval of time to elapse wherein the oxidized redox moiety of the oxidized compound is irreversibly reduced by endogenous reducing agents to form a reduced compound in the test sample when the tissue is deprived of oxygen;
c) irradiating the sample with NIR radiation; and
d) detecting a photoacoustic signal from the sample wherein the reduced compound emits a photoacoustic signal;

thereby detecting the presence of hypoxia when present in the sample.

In some embodiments of the above method, step d) further comprises detecting a lack of a photoacoustic signal, wherein the lack of a photoacoustic signal results from a lack of the reduced compound in the test sample, wherein oxidized compound remaining in the test sample emits no photoacoustic signal or a weak photoacoustic signal.

Results

Design and Synthesis.

The development of hypoxia-responsive imaging probes has focused primarily on the use of the 2-nitroimidazole moiety. This functionality has been applied to numerous fluorescence-based probes as well as several $^{18}$F and $^{99}$Tc-labeled radiotracers for PET and SPECT, respectively. The mechanism of activation for these compounds relies on two subsequent one-electron reductions performed by nitroreductases. The first of these reductions produces a nitro radical anion, which can be rapidly reoxidized to the parent nitro compound by molecular oxygen. However, in the absence of oxygen, the nitro radical anion can undergo further reduction to form reactive intermediates that are susceptible to attack by intracellular nucleophiles, resulting in irreversible cross-linking (FIG. 1a). Despite the many examples of this strategy for hypoxia targeting, its application for PA probe design faces several drawbacks. First, the various reduced intermediates that form can have distinct PA properties, which may produce ambiguities in the signal detected. Second, although one-electron reductases are primarily responsible for the reductive activation of these compounds, reduction can also occur via two-electron pathways in an oxygen-independent manner, resulting in false positive signals. Oxygen-independent reduction can also be achieved by bacterial nitroreductases and analogous enzymes found in the mitochondria, providing additional sources of non-specific activation. Finally, reductive activation of 2-nitroimidazole compounds is most commonly associated with chronic rather than acute hypoxia, limiting its application to certain models.

The N-oxide-based trigger of HyP-1 presents a unique, alternative strategy. First reported by Sugiura, et. al. (*Pharmacol. Exp. Ther.* 200, (1977)), the mechanism of oxygen dependency for the bioreduction of N-oxides relies on competitive binding of oxygen to the haem iron of various CYP450 enzymes. In the absence of oxygen, the N-oxide can bind and undergo irreversible two-electron reduction. This design therefore precludes redox cycling and formation of various intermediates, thus minimizing false positives. In addition to a hypoxia-responsive trigger, the PA probe design requires several other important considerations such as high absorptivity, absorbance in the NIR window (650-900 nm) and extensive photostability. The aza-BODIPY dye platform has been shown in recent work to possess these key features (*J. Am. Chem. Soc.* 137, 15628). For the design of HyP-1, an unsymmetric aza-BODIPY containing a hypoxia-responsive trigger on one side and a methoxy substituent on the other (FIG. 1b) was prepared.

As shown in Scheme 1, the synthesis of HyP-1 began with the preparation of key building blocks 3 and 4. This was accomplished via Claisen-Schmidt condensation of benzaldehyde and the corresponding acetophenone precursor, followed by 1,4-addition of the nitromethane anion. Heterodimerization of 3 and 4 provided tetraarylazadipyrromethene 5 in 24% yield. Compound 5 was then treated with $BF_3 \cdot OEt_2$ in the presence of diisopropylethylamine to form the aza-BODIPY core of red-HyP-1 in 85% yield. Finally, oxidation of the aniline to the N-oxide with m-CPBA afforded HyP-1 in 47% yield.

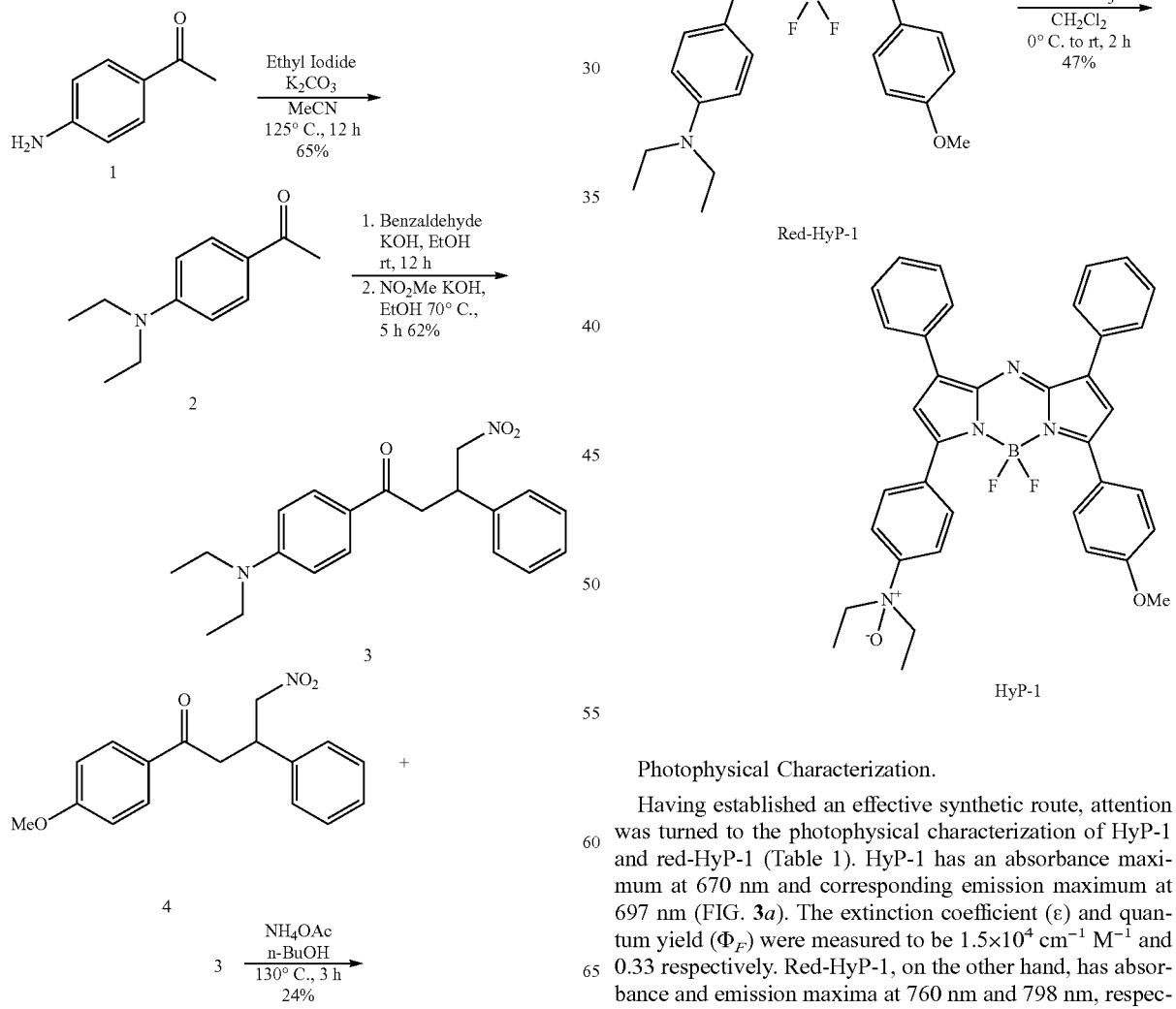

Scheme 1. Synthesis of HyP-1 and red-HyP-1. Red-HyP-1 was obtained via heterodimerization of key precursors 3 and 4, followed by $BF_2$ incorporation using $BF_3 \cdot OEt_2$. HyP-1 was obtained via oxidation of red-HyP-1 using m-CPBA.

Photophysical Characterization.

Having established an effective synthetic route, attention was turned to the photophysical characterization of HyP-1 and red-HyP-1 (Table 1). HyP-1 has an absorbance maximum at 670 nm and corresponding emission maximum at 697 nm (FIG. 3a). The extinction coefficient ($\varepsilon$) and quantum yield ($\Phi_F$) were measured to be $1.5 \times 10^4$ cm$^{-1}$ M$^{-1}$ and 0.33 respectively. Red-HyP-1, on the other hand, has absorbance and emission maxima at 760 nm and 798 nm, respectively. Importantly, red-HyP-1 exhibits an increase in the extinction coefficient ($\epsilon=5.4\times10^4$ cm$^{-1}$ M$^{-1}$) and decrease in quantum yield ($\Phi_F=0.15$), both of which favour an enhanced PA signal (vide infra).

TABLE 1

Photophysical properties of HyP-1 and Red-HyP-1 measured in CHCl3.

| Compound | $\epsilon$ (M$^{-1}$ cm$^1$) | $\lambda_{abs}$ (nm) | $\lambda_{em}$ (nm) | $\Phi_F$ |
|---|---|---|---|---|
| HyP-1 | $1.4 \times 10^4$ | 670 | 697 | 0.33 |
| Red-HyP-1 | $5.4 \times 10^4$ | 760 | 798 | 0.15 |

Figure 3:
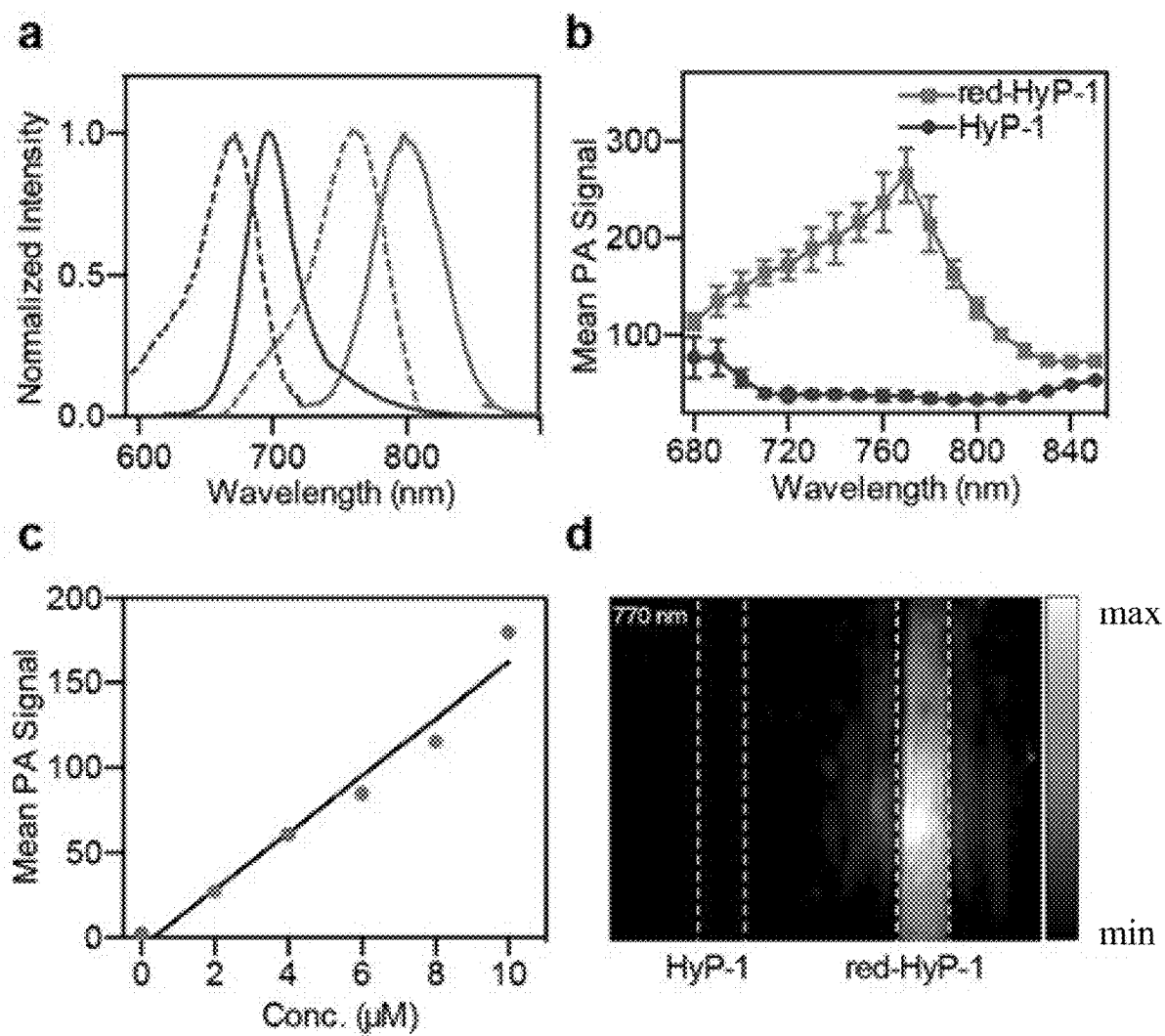
FIG. 3. Photophysical characterization of HyP-1 and red-HyP-1. (a) Normalized absorbance (dashed) and emission (solid) spectra of HyP-1 (left) and red-HyP-1 (right). (b) PA spectra of HyP-1 and red-HyP-1. PA images of HyP-1 and red-HyP-1 solutions (10 µM in 0.1 M potassium phosphate buffer (pH 7.4) with 50% EtOH co-solvent) in tissue-mimicking phantoms were obtained, and the mean PA signal corresponding to each compound was plotted as a function of wavelength. Results are presented as mean±SD (n=3). (c) PA signal corresponding to various concentrations of red-HyP-1. (d) PA image (770 nm) of HyP-1 and red-HyP-1 solutions (10 µM in 0.1 M potassium phosphate buffer with 50% EtOH co-solvent) in tissue-mimicking phantom. Dashed lines indicate positioning of FEP tubes.

The significant change in the absorbance profiles of these compounds can be attributed to disruption of the electron donating capability of the aniline in its N-oxide form. This chemical modification is akin to protonation of the aniline, which has been previously shown to result in similar shifts in the absorbance. The 90 nm separation in absorbance is essential to the probes design as it allows us to readily distinguish each species by selective excitation and subsequent detection using both PA and fluorescence imaging. Indeed, the PA spectra recorded for both HyP-1 and red-HyP-1 correlate well with their absorbance profiles and demonstrate that a strong PA signal can be detected from red-HyP-1 at 770 nm in a concentration dependent manner, while no signal is produced by HyP-1 at this wavelength (FIG. 3). Additionally, because HyP-1 and red-HyP-1 have spectrally resolved emission profiles, ratiometric imaging can be performed by determining the ratio of their fluorescence emission intensities. Ratiometric imaging can account for common imaging artefacts such as uneven dye loading and photobleaching, making this a highly attractive feature for both cellular and in vivo imaging.

In Vitro Characterization of HyP-1.

Figure 2:
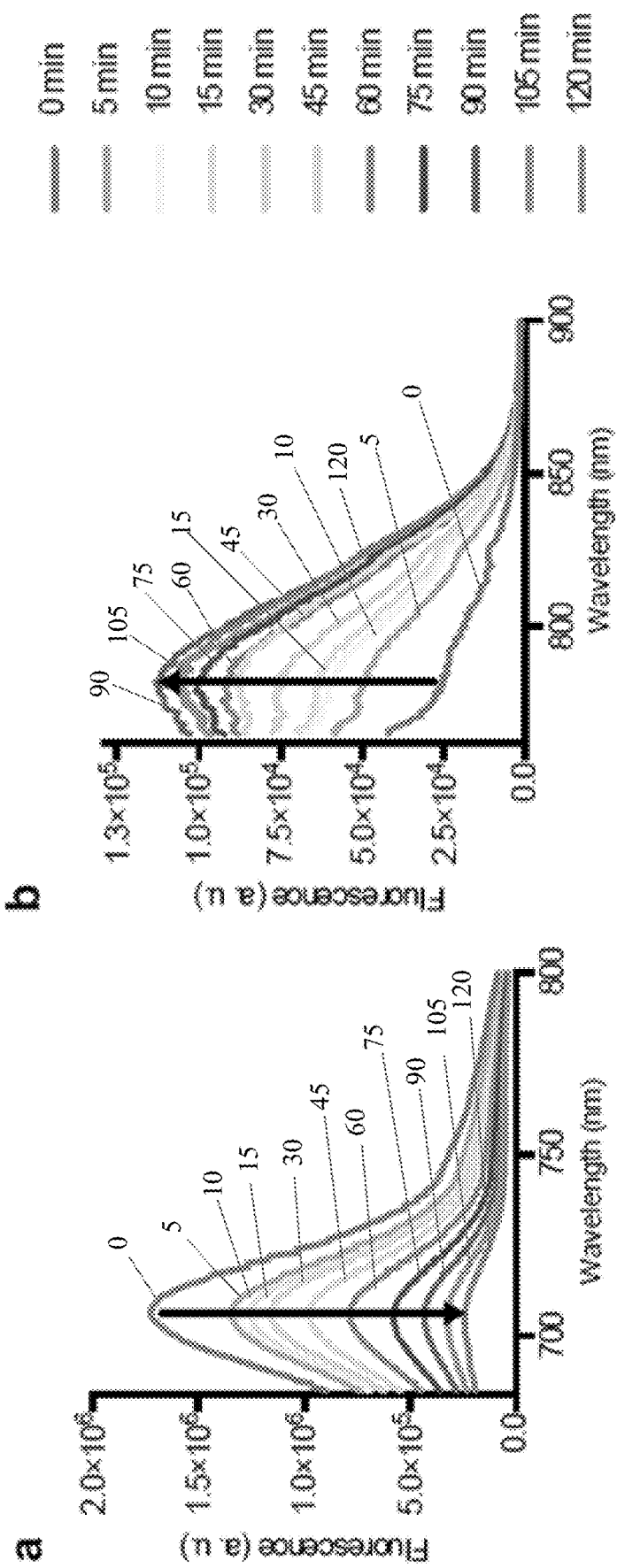
FIG. 2. (a) Time-dependent fluorescence decrease at 710 nm and (b) time-dependent fluorescence increase at 785 nm corresponding to conversion of HyP-1 to red-HyP-1 by rat liver microsomes under hypoxic conditions. HyP-1 (2 µM), rat liver microsomes (10 µL) and NADPH (50 µM) were incubated at 37° C. in degassed 0.1 M potassium phosphate buffer (pH 7.4) under hypoxic conditions, and fluorescence spectra were recorded at the indicated time points. HyP-1 was excited at 672 nm and emission was collected from 685 to 800 nm. Red-HyP-1 was excited at 750 nm and emission was collected from 760 to 900 nm.
Figure 4:
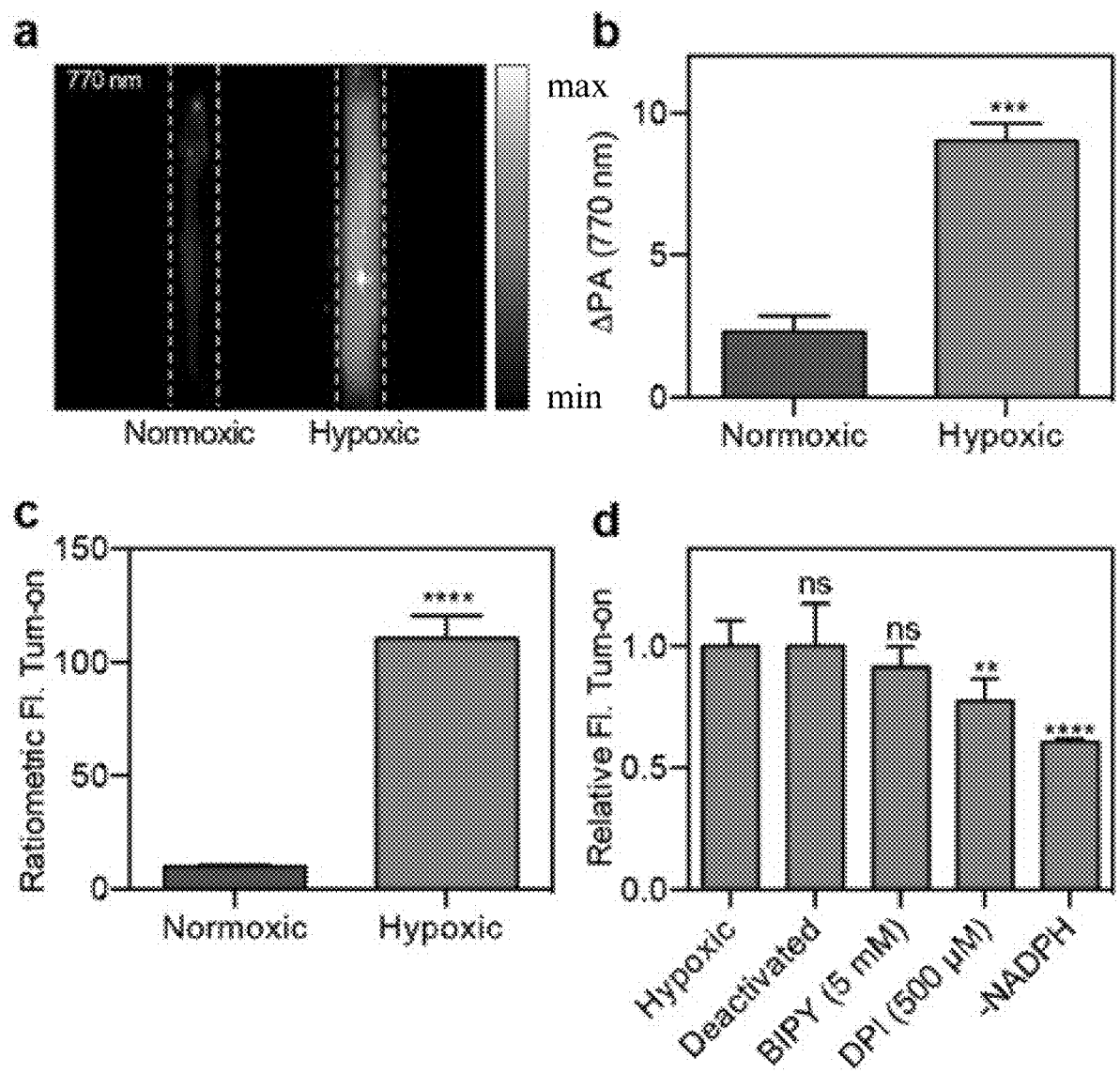
FIG. 4. Hypoxia-selective response of HyP-1 in vitro. (a) Representative PA image (770 nm) of reaction mixtures incubated under normoxic or hypoxic conditions for 2 h, then quenched with an equal volume of acetonitrile. Dashed lines indicate positioning of FEP tubes. (b) Change in PA signal (770 nm) produced after 2 h incubation of HyP-1 (10 µM) with rat liver microsomes (RLM) (200 µg/mL) and NADPH (50 µM) in normoxic and hypoxic conditions (n=3). (c) Ratiometric fluorescence turn-on after 2 h incubation of HyP-1 (2 µM) with RLM (200 g/mL) and NADPH (50 µM) in normoxic or hypoxic conditions (n=3). (d) Normalized fluorescent turn-on after 1 h hypoxic incubation of HyP-1 (2 µM) with RLM (100 µg/mL) and NADPH (50 µM) under various conditions. Statistical significance represents a comparison to the hypoxic control (n=6). Results with error bars are represented as mean±SD. $p<0.01$, *$p<0.001$, ****$p<0.0001$.

The responsiveness of HyP-1 to hypoxia was first evaluated in vitro via fluorescence by incubating HyP-1 with CYP450-rich rat liver microsomes under atmospheric (normoxic) and oxygen-deprived (hypoxic) conditions. Rat liver microsomes are most commonly employed to assess drug metabolism, but have also been extensively used to study the activation of hypoxia-responsive probes and prodrugs. Under hypoxic conditions, a time-dependent fluorescence enhancement at 785 nm and concomitant decrease at 710 nm was observed, indicating complete conversion of HyP-1 to red-HyP-1 with no apparent formation of by-products (FIG. 2). In particular, an authentic solution of red-HyP-1 is identical in appearance (red in colour) and exhibits an emission maximum (785 nm) indistinguishable from that of the RLM reaction mixture. This was further confirmed by mass spectrometry analysis, in which an M+1 peak of 599.2817 corresponding to red-HyP-1 was observed. Overall, an average 105-fold ratiometric turn-on response occurred after hypoxic incubation for 2 hours at 37° C., while only a small 10-fold change in the ratiometric fluorescence resulted from normoxic incubation (FIG. 4c). The PA response of HyP-1 under identical conditions was evaluated by quenching the reaction mixtures with an equal volume of acetonitrile and transferring the solutions into fluorinated ethylene propylene (FEP) tubes, which were inserted into the centre of a 2 cm thick agarose-based tissue-mimicking phantom. Irradiation at 770 nm afforded a 4-fold greater PA signal produced from the hypoxic reaction (FIGS. 4a and 4b).

Figure 8:
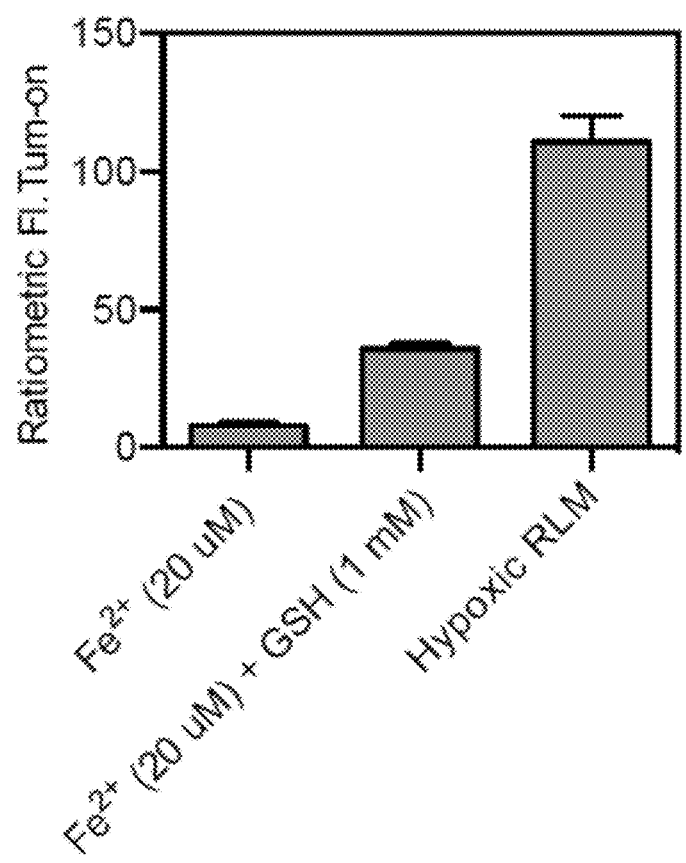
FIG. 8. Ratiometric fluorescence turn-on response of HyP-1 (2 μM) in the presence of $FeSO_4$ (20 μM) and $FeSO_4$ (20 μM)+GSH (1 mM) in 50 mM HEPES buffer (pH 7.4, 0.1% v/v CrEL) after 1 h incubation at 37° C. Turn-on response in the presence of rat liver microsomes under hypoxic conditions shown for comparison.

Fe(II)-mediated reduction of N-oxides has been exploited previously for the development of several fluorescent probes for this metal ion, thus it was critical for us to determine the response of HyP-1 to Fe(II). HyP-1 exhibited a mere 8-fold ratiometric turn-on after a 1-hour incubation in the presence of 20 μM FeSO$_4$ in HEPES buffer (FIG. 8). A more significant turn-on response of 35-fold (one third of the maximum turn-on) was observed when the solution was supplemented with 1 mM GSH, indicating that Fe(II) is capable of converting HyP-1 to red-HyP-1 under these conditions. However, because intracellular concentrations of free iron are low due to sequestration by ferritin, this was not anticipated to be a major source of HyP-1 activation in vivo.

It was hypothesized that the reduction of HyP-1 by hypoxic rat liver microsomes is due to haem-based redox proteins such as CYP450 enzymes, a process that has been previously reported for various N-oxide-containing compounds. However, it has also been shown that Fe(II) can be released from ferritin in rat liver microsomes under anaerobic conditions, and given the response of HyP-1 to Fe(II), the factors responsible for HyP-1 reduction in vitro was verified. When an excess of 2,2'-bipyridine (BIPY), an iron chelator, was added to HyP-1 in the presence of rat liver microsomes under hypoxic conditions, no significant inhibition of the turn-on response was observed (FIG. 4d). In contrast, inhibition of HyP-1 reduction was achieved both by the addition of diphenyliodonium chloride (DPI), an inhibitor of CYP450 reductases, and exclusion of NADPH, which is necessary for enzymatic activity. Interestingly, HyP-1 was also converted to red-HyP-1 in the presence of heat-inactivated rat liver microsomes in a manner similar to several previously reported N-oxide containing compounds. These data led us to conclude that microsomal reduction of HyP-1 is independent of labile Fe(II) and relies instead upon both enzymatic and non-enzymatic bioreduction by the haem iron of CYP450 enzymes, as well as other haem-based redox proteins.

Figure 9:
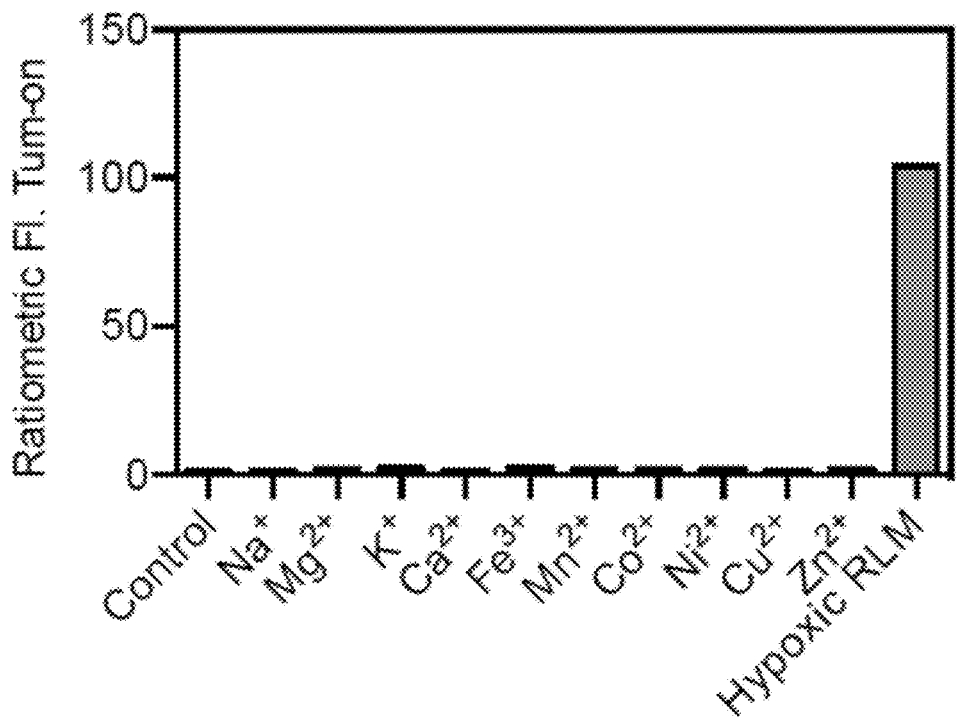
FIG. 9. Ratiometric fluorescent turn-on response of HyP-1 (2 μM) in the presence of various metal ions in 0.1 M potassium phosphate buffer (pH 7.4, 0.1% v/v CrEL) after 2 h incubation at 37° C. Concentrations used were 2 mM for $Na^+$, $Mg^{2+}$, $K^+$ and $Ca^{2+}$, and 50 μM for all other metal ions.
Figure 10:
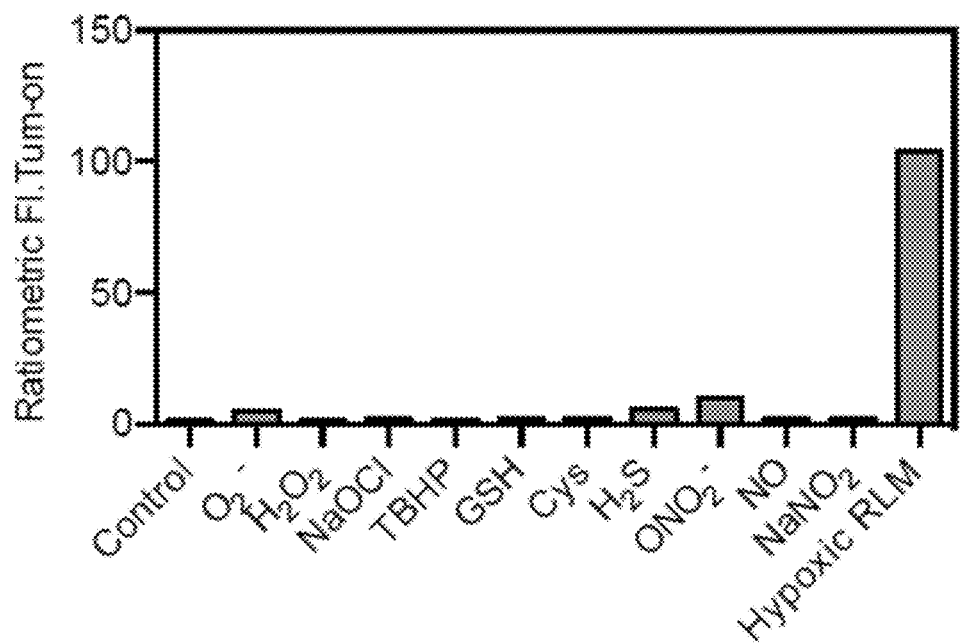
FIG. 10. Ratiometric fluorescence turn-on response of HyP-1 (2 μM) in the presence of various reactive oxygen, nitrogen and sulfur species (100 μM) in 0.1 M potassium phosphate buffer (pH 7.4, 0.1% v/v CrEL) after 2 h incubation at 37° C.
Figure 11:
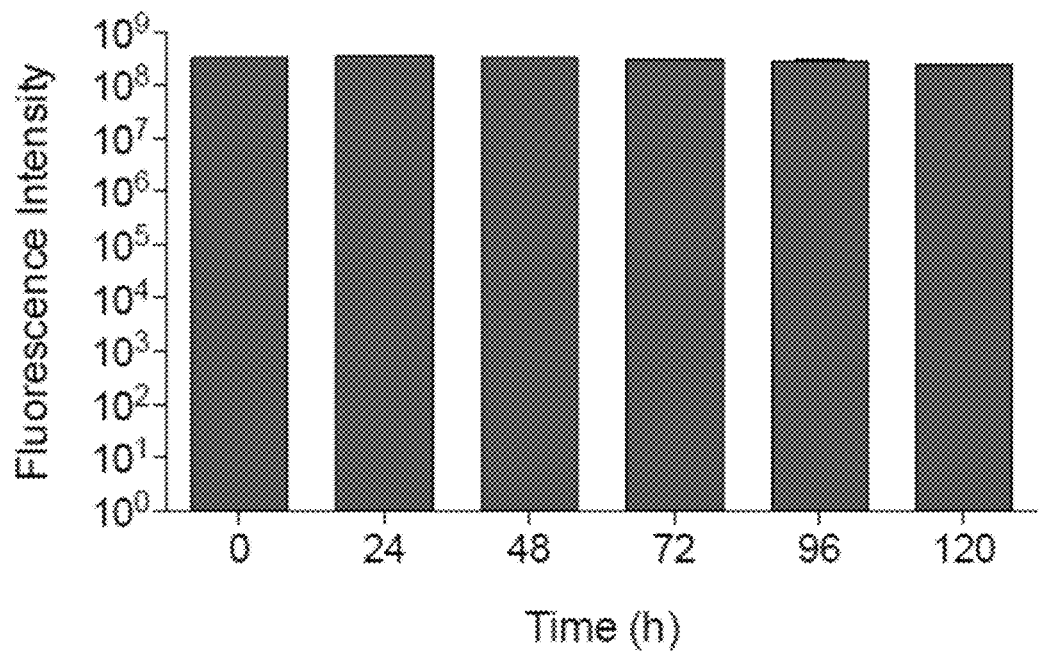
FIG. 11. Fluorescence intensity (Ex.=670 nm) of HyP-1 (2 μM) at the indicated time points during extended incubation in 0.1 M potassium phosphate buffer (pH 7.4, 0.1% v/v CrEL) under ambient light and temperature. Represented as mean±SD (n=3).
Figure 12:
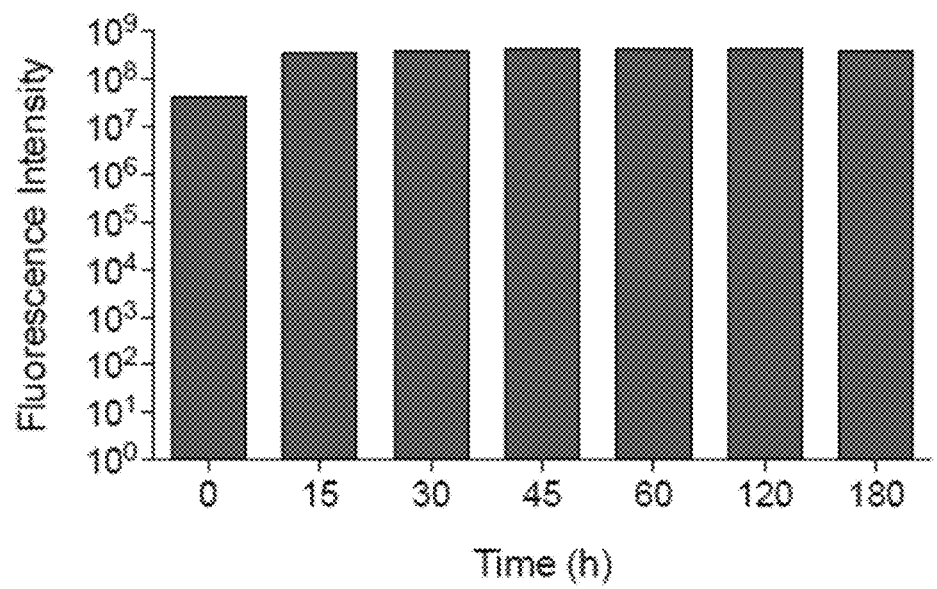
FIG. 12. Fluorescence intensity (Ex.=670 nm) of HyP-1 (2 μM) at the indicated time points during incubation in 0.1 M potassium phosphate buffer (pH 7.4) supplemented with human plasma (20% v/v) at 37° C. for 3 h.
Figure 13:
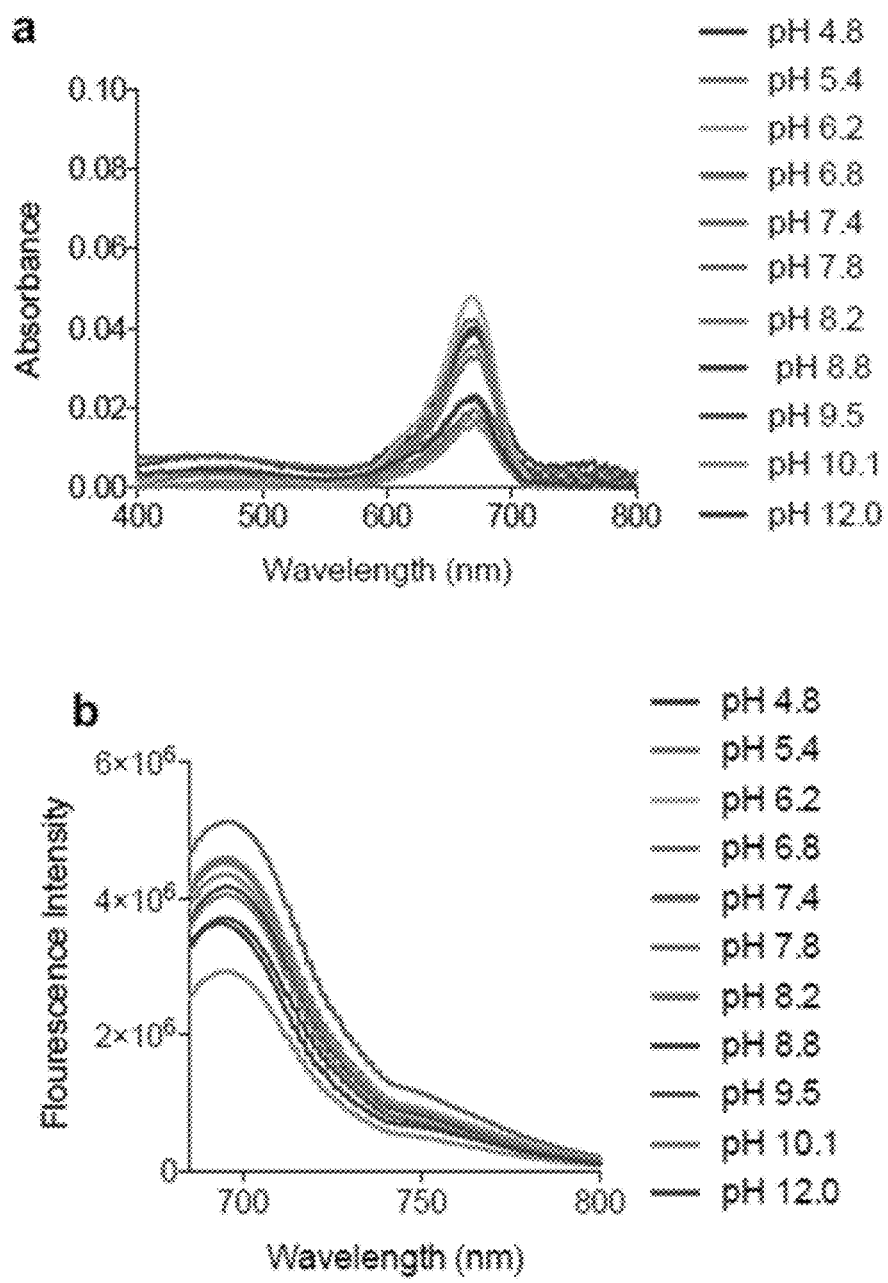
FIG. 13. (a) Absorbance and (b) fluorescence spectra of HyP-1 (2 μM) in 20 mM BRB buffers containing 50% v/v EtOH (pH range 4.8-12.0).
Figure 14:
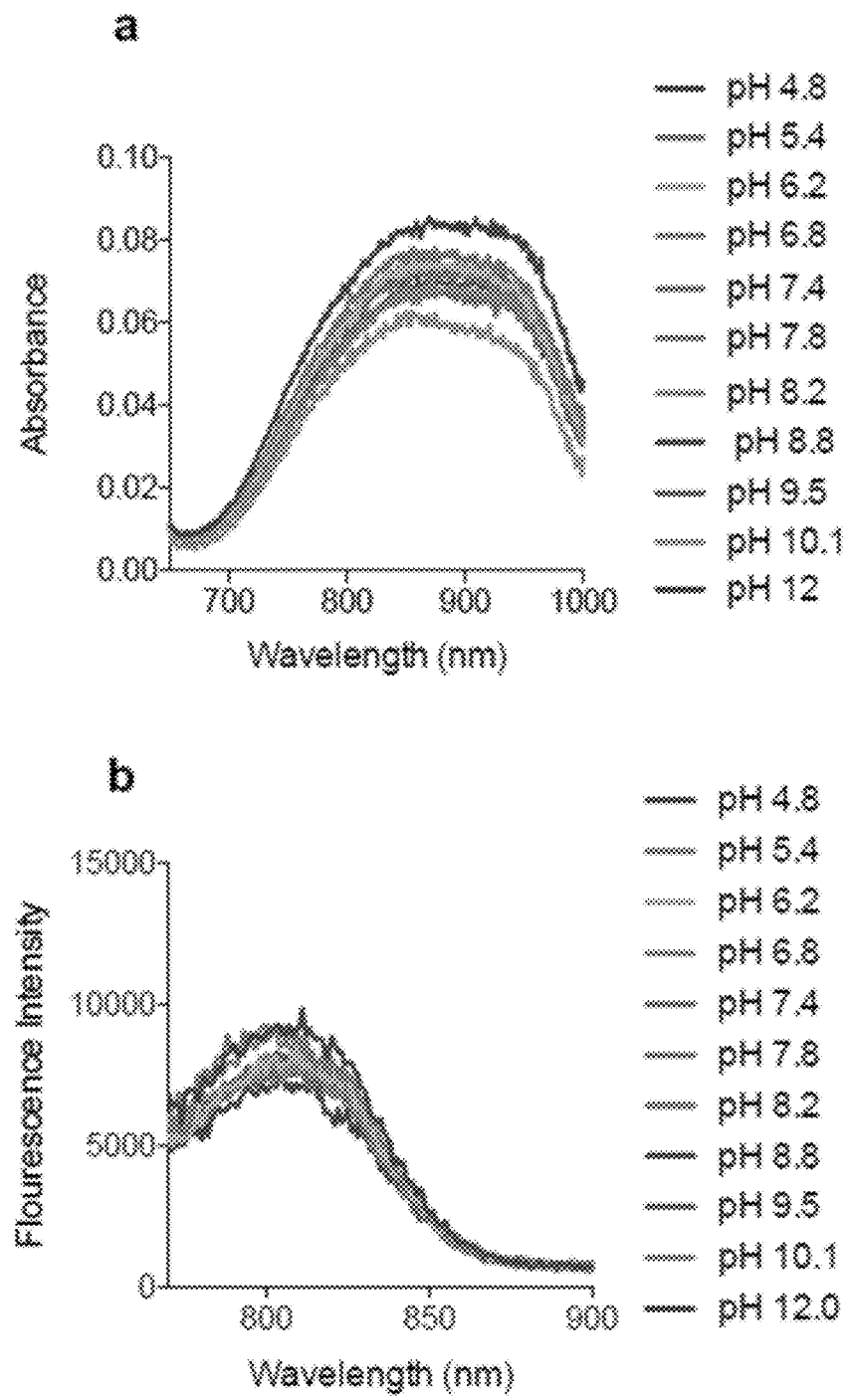
FIG. 14. (a) Absorbance and (b) fluorescence spectra of red-HyP-1 (2 μM) in 20 mM BRB buffers containing 50% v/v EtOH (pH range 4.8-12.0).
Figure 15:
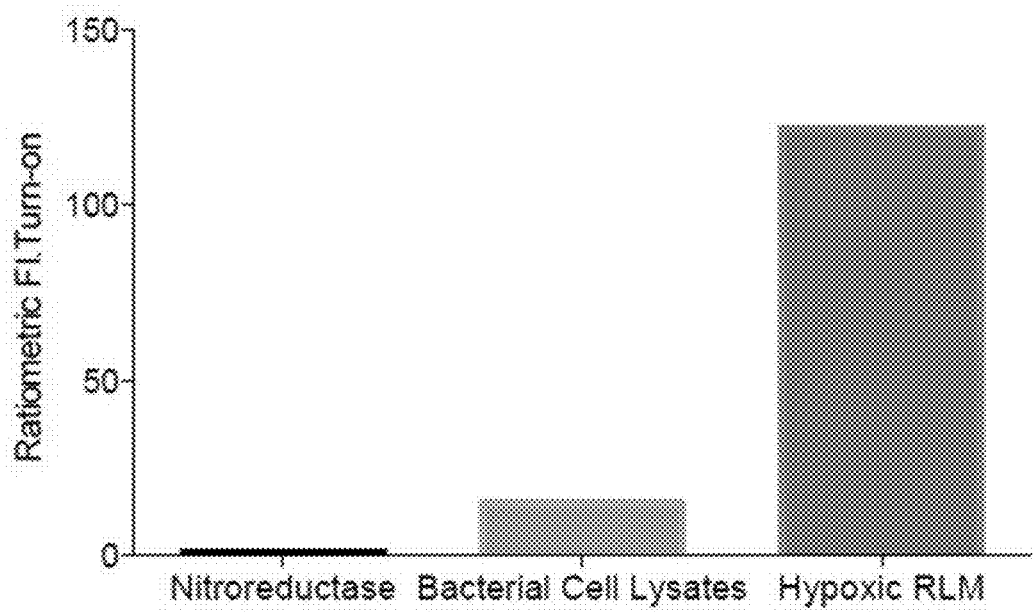
FIG. 15. Ratiometric fluorescence turn-on of HyP-1 in the presence of purified nitroreductase enzyme and bacterial cell lysates in comparison to turn-on observed in the presence of rat liver microsomes under hypoxic conditions. For the nitroreductase experiment, HyP-1 (2 μM) was incubated in the presence of nitroreductase (0.5 μg/mL) and NADH (100 μM) in 0.1 M potassium phosphate buffer (pH 7.4) at 37° C. for 2 h. For the bacterial experiment, bacteria were grown overnight, and cells were lysed via sonication. The suspension was centrifuged at 4000 rpm for 10 min, and the supernatant was removed. HyP-1 (2 μM) was incubated with cell lysate solution (1 mL) at 37° C. for 2 h.
Figure 16:
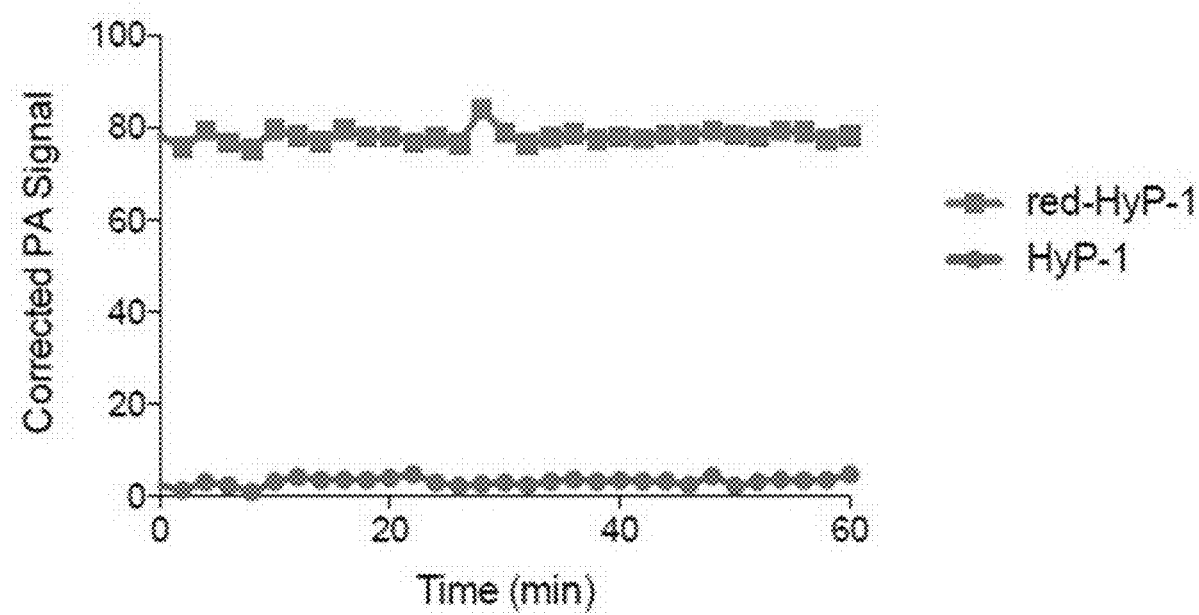
FIG. 16. PA signal (770 nm) at the indicated time points of HyP-1 (dots) and red-HyP-1 (squares) solutions (10 μM in 0.1 M potassium phosphate buffer with 50% v/v EtOH) produced upon continuous image acquisition over the course of 1 h. Reported values represent mean PA signal observed after subtracting background signal produced from tissue-mimicking phantom.

In addition to Fe(II), the response of HyP-1 to a variety of alkali, alkaline earth and transition metals was also determined. No significant turn-on was observed, verifying the stability of HyP-1 under these experimental conditions (FIG. 9). Likewise, treatment of HyP-1 with a variety of reactive oxygen, nitrogen and sulphur species commonly encountered in the cellular environment yielded similar results (FIG. 10). To further evaluate the stability of HyP-1, a 10 μM solution of the probe was exposed to ambient light and temperature for up to 5 days. Additionally, a 10 μM solution of HyP-1 supplemented with human plasma was incubated at 37° C. for 3 hours. During these experiments, no substantial decomposition of HyP-1 was observed, demonstrating its exceptional chemostability (FIGS. 11 and 12). Furthermore, the absorbance and emission spectra of HyP-1 and red-HyP-1 in buffers ranging in pH from 4.8 to 12.0 revealed no significant pH dependence (FIGS. 13 and 14). As mentioned previously, a major limitation of 2-nitroimidazole-based hypoxia probes is their susceptibility to oxygen-independent reduction via two-electron processes, such as by bacterial nitroreductases. When HyP-1 was incubated with either purified bacterial nitroreductase or E. coli cell lysates, minimal conversion to red-HyP-1 was observed (FIG. 15). Finally, the photostability of both HyP-1 and red-HyP-1 was evaluated via continuous PA image acquisition at 770 nm over the course of 1 hour. The PA intensities of both sample solutions remained unchanged during this time, demonstrating the excellent photostability of both compounds (FIG. 16).

Detecting Hypoxia in Living Cells with HyP-1.

Figure 5:
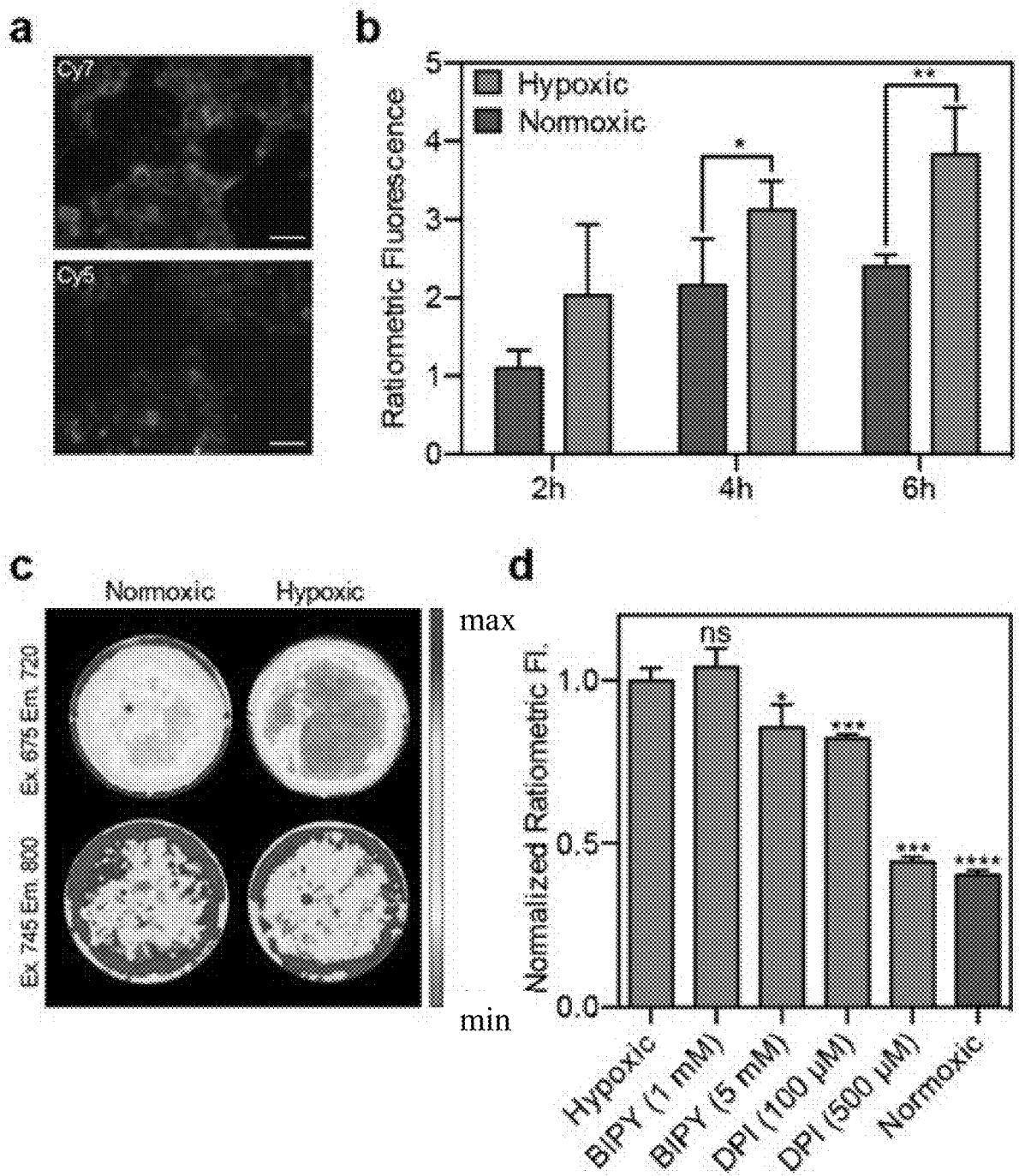
FIG. 5. Ratiometric fluorescence imaging of HyP-1 in hypoxic cell culture. (a) Representative images (scale bar represents 50 µm) and (b) quantification of time-dependent ratiometric fluorescence of 4T1 cells stained with 5 µM HyP-1 in serum-free medium and incubated under hypoxic or normoxic conditions. Ratios determined by dividing Cy7 emission by Cy5 emission (n=4). (c) IVIS Spectrum images of 4T1 cells stained with HyP-1 (5 µM) and incubated under normoxic or hypoxic conditions for 4 h. (d) Normalized ratiometric fluorescence of 4T1 cells stained with HyP-1 (5 µM) under various hypoxic or normoxic conditions. Statistical significance represents a comparison to the hypoxic control. Results with error bars are represented as mean±SD. *$p<0.05$, $p<0.01$, *$p<0.001$, ****$p<0.0001$.

After establishing excellent selectivity and responsiveness to hypoxic conditions in vitro, the performance of HyP-1 in living cells was evaluated before moving to in vivo studies. 4T1 murine mammary carcinoma cells were treated with a 5 M solution of HyP-1 and incubated at 37° C. either in a standard atmosphere containing 20% oxygen (normoxic conditions), or in an airtight chamber containing <0.1% oxygen (hypoxic conditions). Imaging was performed at 2, 4 and 6 hours using an epifluorescence microscope equipped with Cy5 and Cy7 filter sets to visualize HyP-1 and red-HyP-1, respectively (FIG. 5a). Cells incubated under hypoxic conditions exhibited a time-dependent ratiometric fluorescence response that was 1.6-fold higher than the normoxic control after 6 hours (FIG. 5b).

Figure 17:
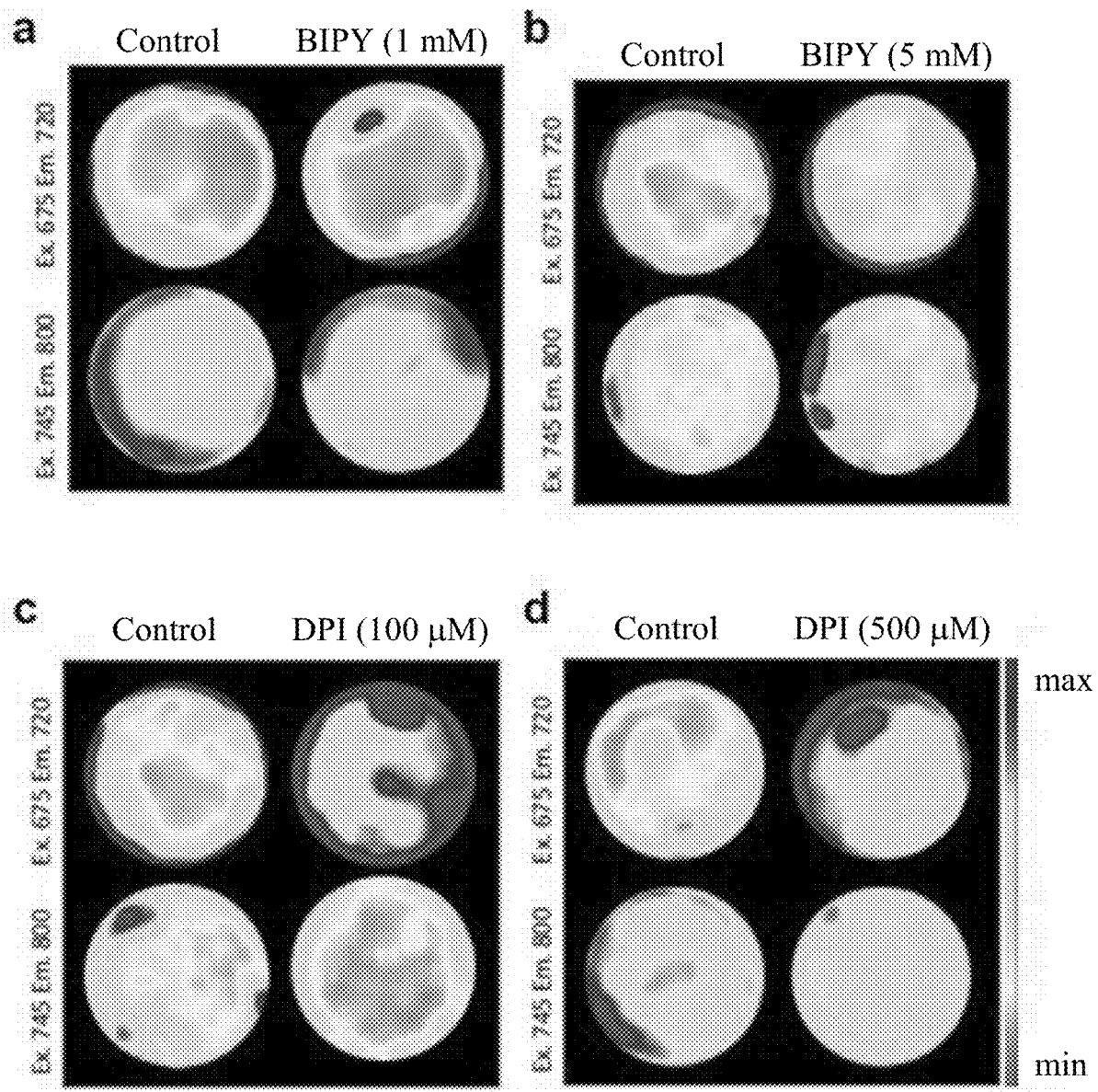
FIG. 17. Representative IVIS spectrum images of 4T1 cells plated on 6-well plates and treated with serum-free medium containing HyP-1 (5 μM) and (a) BIPY (1 mM) (b) BIPY (5 mM) (c) DPI (100 μM) and (d) DPI (500 μM). Cells were incubated under hypoxic conditions for 4 hours prior to imaging. Images were acquired using 675/720 and 745/800 excitation/emission filter sets to visualize HyP-1 and red-HyP-1, respectively. A vehicle control for each condition is shown for comparison.

Ratiometric fluorescence imaging was also performed on 4T1 cells cultured in 6-well plates using an IVIS Spectrum imaging system. Cells were stained with a 5 µM solution of HyP-1 and incubated in either normoxic or hypoxic conditions for 4 hours (FIG. 5c). The ratiometric response of the hypoxic wells was found to be 2.5-fold higher than the normoxic response (FIG. 5d). To further verify the in vitro results and determine the cellular factors responsible for HyP-1 reduction, cells were also stained with HyP-1 solutions containing either BIPY or DPI at multiple concentrations and incubated under hypoxic conditions. The presence of 1 mM BIPY had no effect on the cellular response to HyP-1, while 5 mM BIPY resulted in only slight reduction of the ratiometric fluorescence. On the other hand, incubation with DPI resulted in significant dose-dependent inhibition, again implicating the role of haem-based redox proteins such as CYP450 enzymes in the reduction of HyP-1 (FIG. 5d and FIG. 17).

In Vivo Imaging of a Hypoxic Tumour-Bearing Mouse Model.

To evaluate the utility of HyP-1 for visualization of intratumoural hypoxia, a murine mammary carcinoma tumour model that has been previously utilized for evaluating hypoxia-responsive probes was employed.

Figure 6:
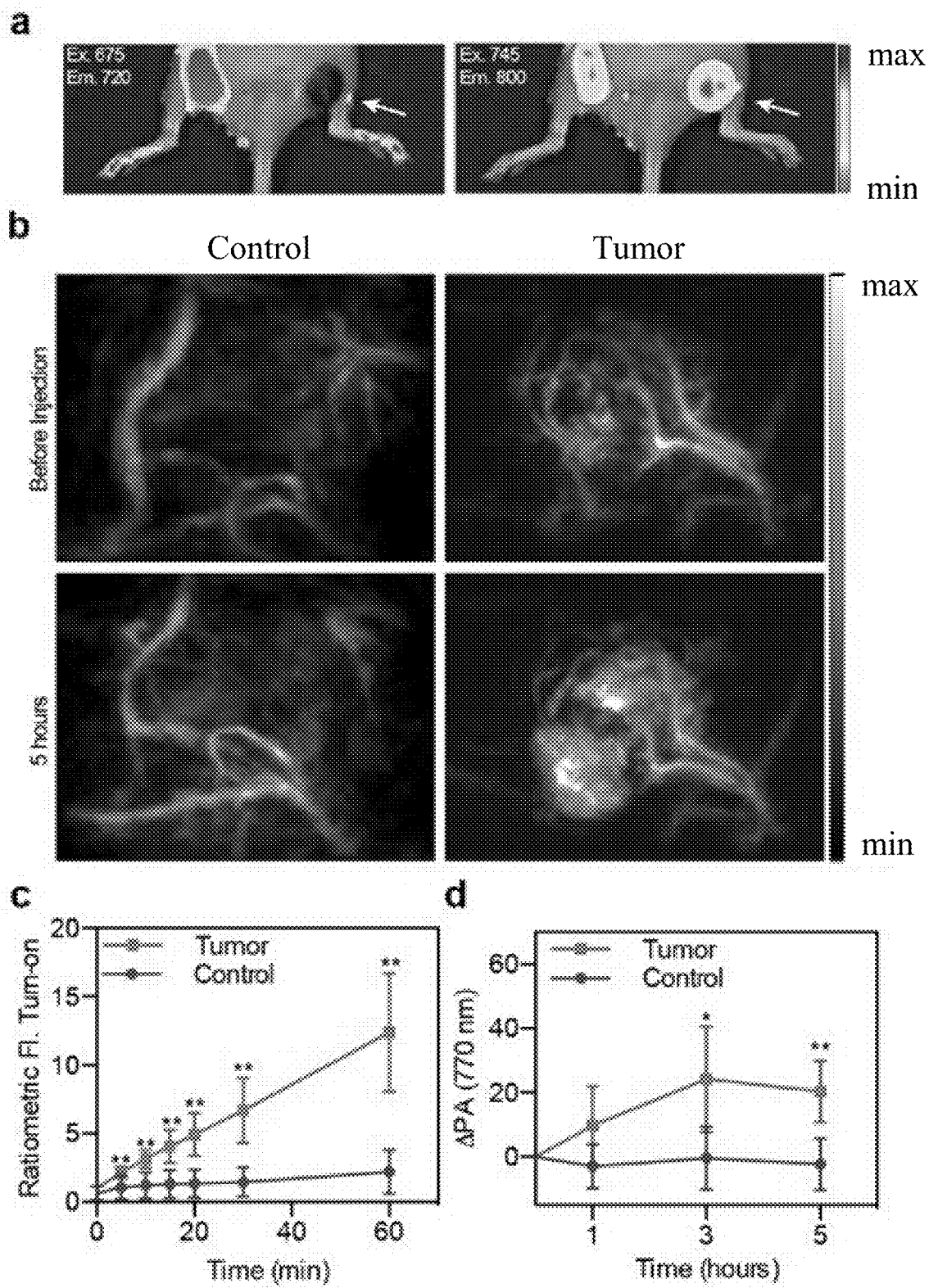
FIG. 6. In vivo imaging of tumour hypoxia with HyP-1. (a) Fluorescence (IVIS Spectrum) images acquired of a 4T1 tumour-bearing mouse 1 h following intratumoural injection (50 μL, 100 μM) of HyP-1. Images were acquired using 675/720 nm and 745/800 nm filter sets. Arrows indicate tumour. (b) PA images (770 nm) of the tumour-bearing and control flank before and 5 h following injection of HyP-1 (50 μL, 0.3 mg/kg). Scale bar represents 2 mm. (c) Time-dependent ratiometric fluorescence increase of tumour-bearing and control flanks (n=5). (d) Time-dependent increase of PA signal of tumour-bearing and control flanks (n=5). Results with error bars are represented by mean±SD. *p<0.05, **p<0.01.

Tumour allografts were generated via subcutaneous implantation of 4T1 cells into the right flanks of BALB/c mice. The tumours were allowed to grow to volumes of 300-400 mm$^3$ prior to imaging. As an initial study to visualize the intratumoural conversion of HyP-1 to red-HyP-1 in real time, ratiometric fluorescence imaging was performed immediately following administration of HyP-1 (50 µL, 100 µM) via intratumoural or subcutaneous (control) injection. After 1 hour, the average ratiometric fluorescent turn-on was 5.6-fold greater in the tumour tissue, demonstrating the hypoxia-selective response of HyP-1 (FIGS. 6a and 6c).

Next, attention was turned to the application of HyP-1 for hypoxia detection using PA imaging. HyP-1 (50 µL, 0.3 mg/kg) was administered to tumour-bearing mice intravenously via tail vein injection, and PA images of both the tumour-bearing and control flanks were acquired at 1, 3 and 5 hours following injection. An average mean PA signal increase of 20.5 (a.u.) was observed in the tumour tissue, while no increase was observed in the control flank (FIGS. 6b and 6d). The 3D-reconstructions of the PA images enabled visualization of specific areas within the tumour where signal was highest, a significant improvement compared to the minimally resolved signal obtained using fluorescence imaging (FIG. 6b). It was hypothesized that these areas of high intensity correlate with the highest concentrations of red-HyP-1, and therefore with regions of most severe hypoxia. These results demonstrate the superior resolution achievable in deep tissue using PA imaging, as well as the utility of HyP-1 for hypoxia detection following systemic administration.

In Vivo Imaging of a Murine Hindlimb Ischemia Model.

Figure 7:
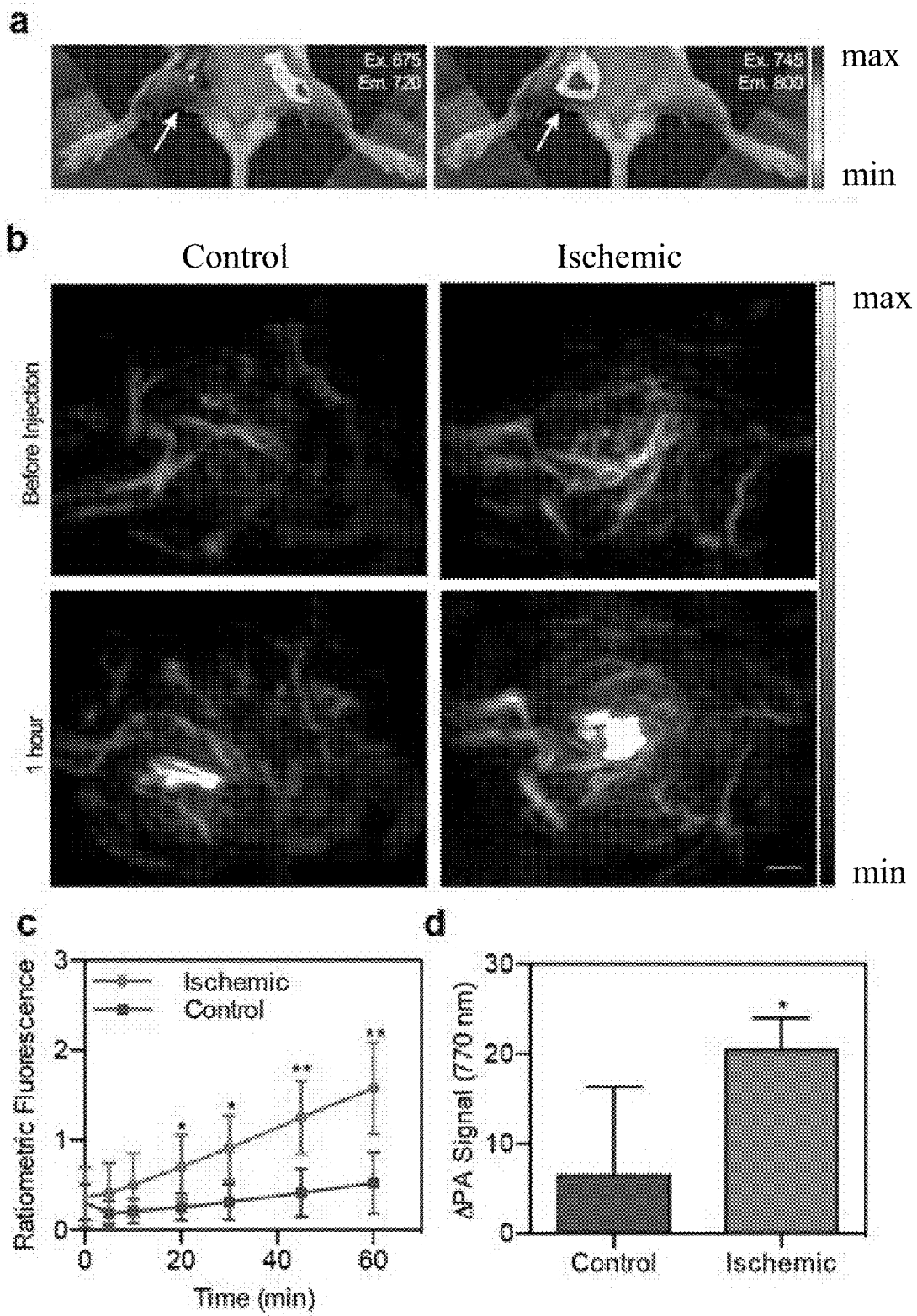
FIG. 7. In vivo imaging of a murine hindlimb ischemia model with HyP-1. (a) Fluorescence (IVIS Spectrum) images acquired of hindlimb ischemia mouse model (right leg) 1 h following intramuscular injection (50 μL, 50 μM) of HyP-1 in both legs. Images were acquired using 675/720 nm and 745/800 nm filter sets. Mouse imaged in supine position; arrows indicate ischemic tissue. (b) PA images (770 nm) of the ischemic and control leg before and 1 h following injection of HyP-1 (50 μL, 50 μM). Scale bar represents 2 mm. (c) Time-dependent ratiometric fluorescence increase of ischemic and control limbs (n=5). (d) Time-dependent increase of PA signal of ischemic and control limbs (n=4). Results with error bars are represented as mean±SD. *p<0.05, **p<0.01.
Figure 18:
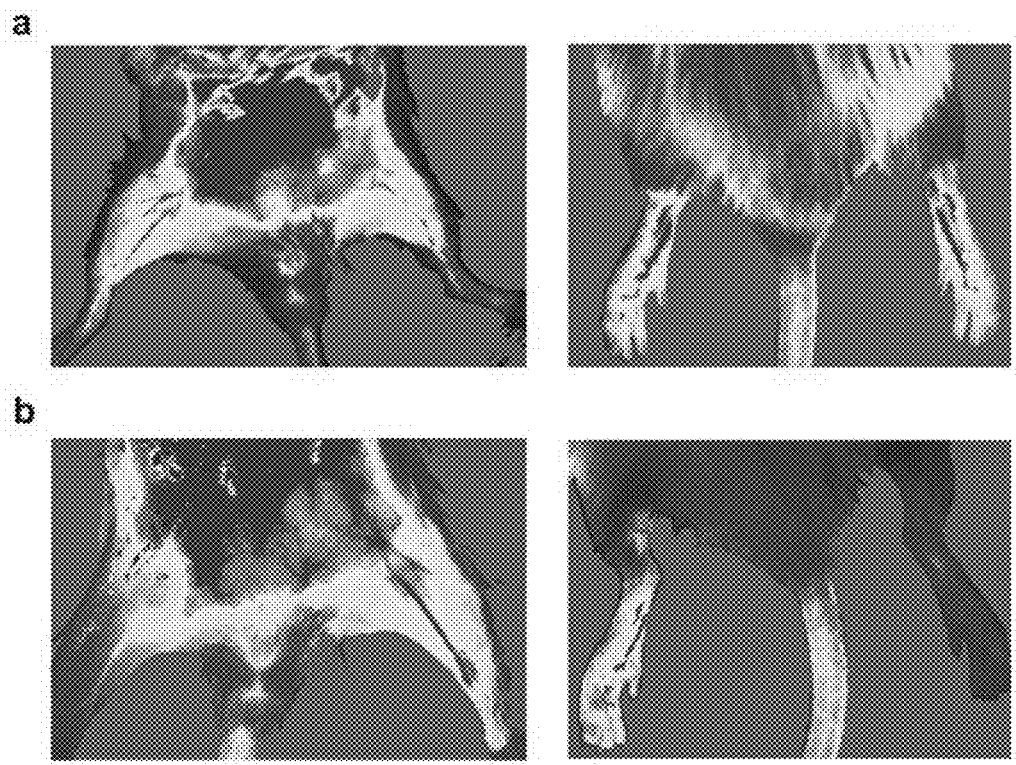
FIG. 18. Laser Doppler perfusion images acquired (a) before and (b) 15 minutes after surgical ligation of the femoral artery in the right hindlimb.
Figure 19:
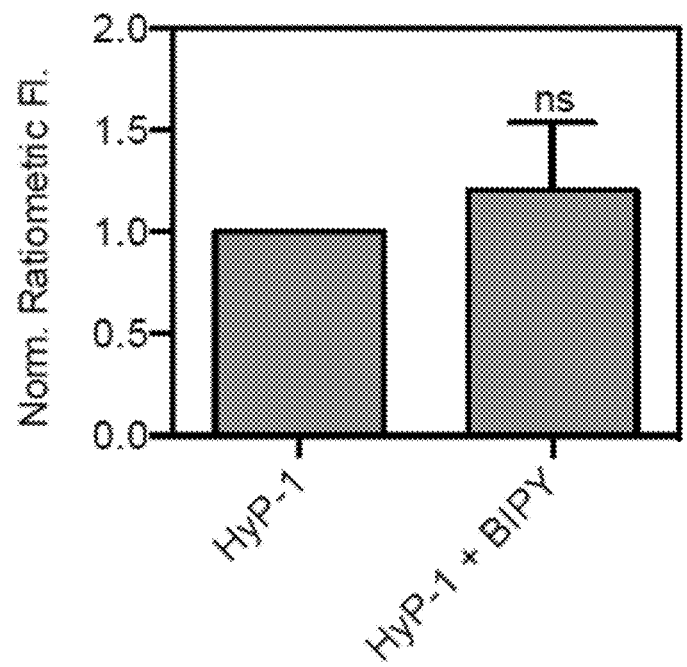
FIG. 19. Normalized ratiometric fluorescence of ischemic hindlimbs following intramuscular injection of HyP-1 (50 μL, 50 μM) or HyP-1+BIPY (5 mM). Surgical ligation of the femoral artery was performed on both hindlimbs of female BALB/c mice (6 weeks old). HyP-1 was injected intramuscularly into one of the hindlimbs, while a HyP-1 solution containing BIPY was injected into the other hindlimb. Images were acquired using 675/720 nm and 745/800 nm filter sets. Ratiometric fluorescence of the BIPY-treated hindlimb was normalized with respect to the control. Results are presented as mean±SD (n=3).

To visualize the response of HyP-1 in a model of rapidly developing hypoxia, a murine hindlimb ischemia model of peripheral artery disease was employed. Ischemia was induced in the right hindlimb of BALB/c mice via ligation of the femoral artery. To confirm that the ligation had successfully limited blood perfusion through the limb, laser Doppler perfusion imaging was performed immediately following the surgery, and a drastic decrease in blood flow was observed in the right leg (FIG. 18). After a 1-hour recovery period, HyP-1 (50 µL, 50 µM) was administered via intramuscular injection into both hindlimbs of the mouse. To visualize the time-dependent response of HyP-1 in the ischemic and non-ischemic tissue, ratiometric fluorescence imaging was performed over the course of 1 hour immediately following injection. A rapid increase in the ratiometric fluorescence intensity corresponding to conversion of HyP-1 to red-HyP-1 was observed in the ischemic tissue. Overall, the average ratiometric signal was 3-fold greater in the ischemic tissue compared to the control, indicating oxygen-dependent inhibition of HyP-1 activation (FIGS. 7a and 7c). Moreover, it was confirmed that the activation of HyP-1 under ischemic conditions does not involve Fe(II) by co-administering HyP-1 with BIPY (5 mM) to chelate free Fe(II). The ratiometric fluorescence enhancement was statistically indistinguishable from that of when HyP-1 was administered alone (FIG. 19).

After observing the hypoxia-mediated response of HyP-1 in the hindlimb ischemia model, attention was turned to detecting this response using PA imaging. As described above, surgical ligation was employed to induce ischemia, and HyP-1 (50 µL, 50 µM) was administered via intramuscular injection. PA images were acquired 1 hour following injection, and a robust signal enhancement 3.1-fold greater on average than that of the control leg was observed in the ischemic tissue (FIGS. 7b and 7d). These results demonstrate that HyP-1 can be applied to hypoxia detection in multiple disease models. Additionally, the limited time frame between induction of ischemia and imaging suggests that HyP-1 does not rely significantly on upregulation of haem-based redox proteins, but rather can undergo rapid conversion to red-HyP-1 under hypoxic conditions at constitutive enzyme expression levels.

DISCUSSION

As described above, a hypoxia-responsive imaging agent for PA imaging was designed and evaluated. HyP-1 features a hypoxia-responsive trigger that enables rapid and direct conversion of an N-oxide to the corresponding aniline, preventing formation of intermediates that may introduce signal ambiguities. Because this design relies primarily on competitive binding of oxygen rather than oxygen-dependent redox cycling, minimal background results from oxygen-independent reduction pathways. As such, this strategy presents a unique alternative for the design of various hypoxia-responsive probes.

The design of small-molecule PA probes relies on the ability of the activated probe to produce a detectable PA signal enhancement compared to the unactivated probe. This can occur via one of several mechanisms, including (1) increasing molar absorptivity, thus increasing the amount of incident light absorbed, (2) decreasing quantum yield, resulting in a greater proportion of non-radiative decay or (3) shifting the absorbance such that irradiation at a certain wavelength produces signal from only the activated probe. Hypoxia-mediated activation of HyP-1 facilitates a turn-on response using all three of these mechanisms. Specifically, conversion of HyP-1 to red-HyP-1 results in a 3.6-fold increase in extinction coefficient, a 2.2-fold decrease in quantum yield and a 90 nm shift in absorbance. Together, these features enable hypoxia detection using PA imaging with high sensitivity and reliability with minimal background.

Although HyP-1 was designed primarily for PA imaging, its NIR absorbance and emission profiles enable ratiometric NIR fluorescence imaging of hypoxia in cellular systems with fluorescence microscopy, followed by direct translation to in vivo models. The absorbance of endogenous chromophores (e.g., haemoglobin) is minimized within the NIR window, thus the development of NIR absorbing probes enables maximum light penetration using optical imaging methods. Therefore, HyP-1 and red-HyP-1 can both be easily visualized in vivo using whole-body NIR fluorescence imaging. Although minimal resolution is achieved, this capability of HyP-1 renders it a highly convenient tool for rapid hypoxia detection in preclinical animal models.

Intratumoural hypoxia is a characteristic property of advanced solid tumours and is a key factor associated with increased metastatic potential and poor treatment outcomes. Tumour hypoxia results primarily from the inability of oxygen to diffuse to poorly vascularized areas (diffusion-limited) or temporary obstructions in blood flow that limit oxygen delivery (perfusion-limited). The heterogeneity of solid tumours can result in significant variations in oxygen deficiency from region to region, and although methods for non-invasive hypoxia detection exist, limited resolution and sensitivity produce significant challenges in determining the distribution of hypoxic volumes within a tumour. It was demonstrated that PA imaging with HyP-1 enables 3D visualization of intratumoural hypoxia with excellent resolution. Comparison of PA images acquired before and after HyP-1 administration reveals specific regions of signal enhancement, which correlates to regions of the most severe hypoxia. The superior resolution and imaging depth of PA images compared to fluorescence images indicates the promising outlook of this emerging imaging modality.

PAD is a debilitating condition that affects nearly 10 million individuals in the United States. PAD is characterized by restricted arterial circulation to the limbs, most commonly the legs, resulting from plaque deposition and arterial hardening. The murine hindlimb ischemia model is widely accepted for the study of PAD and has been used in the evaluation of potential treatment options. Due to the rapid oxygen depletion that results from this model, it was envisioned that the model could be used to demonstrate the response of HyP-1 to hypoxic conditions in vivo independent of extensive changes in gene and protein expression levels that can result from prolonged hypoxia in other models (e.g., cancer). Indeed, it was demonstrated that HyP-1 exhibits a rapid turn-on response in murine hindlimb ischemia just 1 hour following surgical ligation of the femoral artery. These results show the excellent sensitivity of HyP-1 to oxygen deficient conditions resulting from ischemia. PAD represents just one of many ischemic conditions in which HyP-1 could be used to detect rapidly developing hypoxia.

Prior to this work, hypoxia detection using optical methods has relied extensively on fluorogenic probes that provide minimal resolution and depth penetration. Through the development of HyP-1, criteria were established for employing optical-based probe designs for translation into powerful PA imaging agents. Probes such as HyP-1 that undergo reaction-based activation to elicit a PA turn-on response can provide a target-specific readout in deep tissue, a direction that was previously exploited only for cell-based fluorescence imaging. While impressive, the advances in PA techniques and instrumentation have been constrained by a shortage of PA probes that can demonstrate target-specific detection. As such, the importance of HyP-1 extends beyond hypoxia detection.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, $5^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Formulations

The compounds described herein can be used to prepare pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Hypoxia Sensing In Vitro

For hypoxic assays only, cuvettes were sealed with septa, then evacuated and filled with $N_2$ (×3) prior to use. Potassium phosphate buffer (0.1 M, pH 7.4) and NADPH (0.5 mM) were degassed with $N_2$ for 30 minutes. For all assays, phosphate buffer (889 μL) rat liver microsomes (200 μg/mL) and HyP-1 (1 μL, 2 mM in DMSO) were added to the cuvette and pre-incubated at 37° C. for 5 minutes. NADPH (100 μL) was added and incubation continued with fluorescence spectra acquisition occurring at the indicated time points. Spectra were acquired according to the following parameters: $\lambda_{ex}$=672, emission range=685-800 nm and $\lambda_{ex}$=750, emission range=760-900 nm. For BIPY and DPI experiments, the compounds were added from stock solutions (1 M BIPY in DMSO and 50 mM DPI in deionized water) following the 5 minute preincubation, and the buffer volume was adjusted such that the total volume in the cuvette was equal to 1 mL. Deactivated microsomes were prepared by heating in a 45° C. water bath for 30 minutes.

Example 2. Cell Culture

Authenticated 4T1 cells were purchased from ATCC. Cells were grown in RPMI 1640 medium supplemented with 10% fetal bovine serum. Cells were cultured at 37° C. in 5% $CO_2$ and 20% 02 for normoxic conditions. Hypoxic cell culture was performed by incubating cells in a sealed container with a Mitsubishi AnaeroPack™ anaerobic gas generator. Hypoxic conditions were verified with the use of a Mitsubishi RT Anaero-Indicator.

Example 3. Fluorescence Imaging in Living Cells

For fluorescence microscopy, cells were plated in 4-well chamber slides at an initial density of $1 \times 10^4$ cells/mL and allowed to grow until 60-80% confluent (approximately 6 days). Media was removed and cells were washed with PBS. A 5 M solution of HyP-1 in serum-free medium was added, and cells were then incubated under hypoxic or normoxic conditions. Images were obtained using Cy5 and Cy7 filter cubes and analysed using ImageJ software (Version 1.50i).

For cellular imaging using the IVIS Spectrum imaging system, cells were plated in a 6-well plate at an initial density of $1.7 \times 10^4$ cells/mL and allowed to grow until 60-80% confluent (approximately 3 days). Media was removed and cells were washed with PBS. A 5 M solution of HyP-1 in serum-free medium was added, and cells were incubated under normoxic or hypoxic conditions for 4 hours. For BIPY and DPI experiments, the staining solution was supplemented with the compound at the appropriate concentration, and ratiometric turn-on was reported relative to a vehicle control. Images were obtained using excitation and emission filter sets of 675/720 nm and 745/800 nm. Regions of interest (ROIs) were drawn around cell-containing wells, and ratiometric signal was calculated by determining the ratio of radiant efficiency corresponding to 800 nm and 720 nm emissions.

Example 4. Murine Tumour Model

All in vivo imaging experiments were performed with the approval of the Institutional Animal Care and Use Committee of the University of Illinois at Urbana-Champaign, following the principles outlined by the American Physiological Society on research animal use. Female mice (5-6 weeks old) were acquired from The Jackson Laboratory. A suspension of $0.5 \times 10^6$ cells in serum-free medium containing 50% v/v matrigel (100 µL) was subcutaneously injected into the right flank of each mouse. Tumours with volumes of 300-400 mm$^3$ formed after 12-15 days. Animals with tumour volumes beyond this range were excluded from analysis.

Example 5. Murine Ischemia Model

All in vivo imaging experiments were performed with the approval of the Institutional Animal Care and Use Committee of the University of Illinois at Urbana-Champaign, following the principles outlined by the American Physiological Society on research animal use. Female mice (5-6 weeks old) were acquired from The Jackson Laboratory. Mice were anesthetized with isoflurane, and unilateral hindlimb ischemia was surgically induced by femoral artery ligation following previously published approaches. Animals that underwent unsuccessful surgery as determined by laser Doppler perfusion imaging were excluded from analysis.

Example 6. Fluorescence Imaging In Vivo

Images were obtained using epi-fluorescence with excitation filters of 675 and 745 and corresponding emission filters of 720 and 800, respectively. Data was processed using Living Image software (Version 4.1). ROIs of equal area were drawn around signals, and the total radiant efficiency in each ROI was determined. Ratiometric signal was calculated by determining the ratio of radiant efficiency corresponding to 800 nm and 720 nm emissions.

Example 7. PA Imaging in Tissue-Mimicking Phantoms

Tissue phantoms were prepared by suspending agarose (4 g) in a solution of 2% milk (2 mL) and deionized $H_2O$ (78 mL). The suspension was then heated in a microwave oven until a viscous gel was produced (30-50 seconds). The gel was transferred to a mold made by drilling holes through a 50 mL centrifuge tube and placing FEP tubes (0.08" diameter) through the holes to create spaces for samples. After cooling the gel for a minimum of 3 hours, the solidified phantom was removed from the mold and cut with a razor blade such that the distance from the sample holes to the phantom's edges was 1.0 cm. To image samples, sample solutions were pipetted into FEP tubing (0.08" diameter, cut to 10 cm long) which was inserted into the phantom and sealed by folding over the ends and securing with additional tubing (0.12" diameter, cut to 5 mm long). Images were acquired using the Step and Shoot mode with 120 angles and 10 pulses per angle. Data was analysed using OsiriX Lite software (Version 8.0). Thick slab processing was used to visualize accumulated signal over 5 mm. ROIs of equal area were drawn around areas containing signal, and mean PA signal in each ROI was recorded.

Example 8. PA Imaging In Vivo

Prior to imaging, hair was removed from the lower body half by shaving and treating with a topical hair removal cream. Mice were positioned on their sides such that the area to be imaged was directly above the light source. Images were acquired using the Step and Shoot mode with 120 angles and 30 pulses per angle. Data was analysed using OsiriX software. Thick slab processing was used to visualize accumulated signal over 12 mm. ROIs of equal area were drawn to include all visible signal in the image, and mean PA signal in each ROI was recorded. Change in PA signal was calculated by subtracting signal from images taken prior to injection from those at given time points.

Example 9. Statistical Analyses

Statistical analyses were performed in GraphPad Prism version 6.0c. Sample sizes in all experiments were sufficiently powered to detect at least a P value <0.05, which was considered to be significant. All data were analysed using Student's T-tests. Data are expressed as mean±SD. Group variances were similar in all cases.

Example 10. Synthesis of HyP-1 and Red-HyP-1

Chemical and Instruments:
4-Aminoacetophenone was purchased from AK Scientific. Ethyl iodide, DIPEA, K2CO3, KOH, $Na_2SO_4$ and NH4OAc were purchased from Oakwood Chemicals. Benzaldehyde, $BF_3 \times OEt_2$, BIPY, DPI, DMSO, m-CPBA, nitroreductase and rat liver microsomes were purchased from Sigma Aldrich. Nitromethane was purchased from Alfa Aesar. Anaero-Indicators, AnaeroPacka anaerobic gas generators, acetonitrile, n-BuOH, CH2Cl2, EtOAc and Hexanes were purchased from Fisher Scientific. $CDCl_3$ was purchased from Cambridge Isotopes Laboratory. Agarose LE was purchased from Gold Biotechnology. NADPH was purchased from EMD Millipore. All chemicals were used as purchased without further purification. Fluorinated ethylene propylene (FEP) tubing (wall thickness 0.01", inner diameters 0.08" and 0.12") were purchased from McMaster-Carr. Thin-layer chromatography (TLC) was performed using glass-backed TLC plates coated with silica gel containing an UV254 fluorescent indicator (Macherey-Nagel). Flash chromatography was performed with 230-400 mesh silica gel P60 (SiliCycle Inc). UV-visible spectra were recorded on a Cary 60 spectrometer. Fluorescence spectra were recorded on a QuantaMaster-400 scanning spectrofluorometer using micro fluorescence quartz cuvettes (Science Outlet). NMR spectra were taken using Bruker or Varian 500 MHz spectrometers at 25° C. High-resolution mass spectra were acquired using Waters Q-Tof Ultima ESI and Waters Synapt G2-Si ESI/LC-MS spectrometers. Cellular imaging was performed using an EVOS FL cell imaging system. In vivo Fluorescence imaging was performed using an IVIS Spectrum CT live-animal imaging system (Perkin-Elmer, USA). PA imaging was performed using an Endra Nexus 128 photoacoustic tomography system (Ann Arbor, Mich., USA).

Data Analysis:
PA images were analysed using OsiriX software (version 8.0). Reported values correspond to mean PA signals in regions of interest (ROIs) of equal area. IVIS Spectrum images were analyzed using Living Image software (version 4.1). Reported values correspond to total radiant efficiency in ROIs of equal area. Statistical calculations (Student's T-test) were performed using GraphPad Prism (version 6.0c).

Buffer Preparation:
0.1 M potassium phosphate buffer (pH 7.4) was prepared by combining stock solutions of $KH_2PO_4$ (1 M, 0.990 mL) and $K_2HPO_4$ (1 M, 4.010 mL) and diluting to a final volume of 50 mL. 20 mM Britton-Robinson (BRB) buffers (pH 4.0-12.0, 50% v/v EtOH) were prepared as described 1. Fine adjustments to pH were made via addition of 0.1 M HCl or 0.1 M NaOH. pH values were determined using a Mettler-Toledo SevenCompact pH meter calibrated using pH 4.0, 7.0 and 10.0 standard buffers at 25° C.

In Vivo Injection Formulations: For all In Vivo Experiments, HyP-1 was Formulated in sterile saline containing 10% DMSO. Sterile saline was prepared by dissolving NaCl (90 mg) in Milli-Q H2O (10 mL) and filtering the resulting solution through a Millex-GS 0.22 µM sterile filter.
Synthetic Methods.

1-(4-(Diethylamino)phenyl)ethan-1-one (2)

To a solution of 4-aminoacetophenone (1) (1.35 g, 10.0 mmol) in MeCN (20 mL) was added ethyl iodide (3.20 mL, 4 equiv.) and $K_2CO_3$ (2.76 g, 2 equiv.). The mixture was heated to 125° C. in a sealed pressure flask overnight, cooled to room temperature and filtered. The filtrate was concentrated and purified by column chromatography (20% EtOAc/Hexanes) to afford the desired compound (1.25 g, 65%) as an off-white solid. $^1$H NMR (500 MHz, CDCl$_3$) δ 7.85 (d, J=8.6 Hz, 2H), 6.62 (d, J=8.8 Hz, 2H), 3.42 (q, J=7.1 Hz, 4H), 2.49 (s, 3H), 1.20 (t, J=6.9 Hz, 6H). $^{13}$C NMR (125 MHz, CDCl$_3$) δ 196.30, 151.36, 131.07, 124.92, 110.33, 44.76, 26.13, 12.75.

1-(4-(Diethylamino)phenyl)-4-nitro-3-phenylbutan-1-one (3)

To a solution of 2 (9.0 g, 47.2 mmol) in EtOH (236 mL) was added benzaldehyde (4.8 mL, 1 equiv.) and aqueous KOH (10 M, 14.2 mL, 3 equiv.). The reaction was stirred overnight at room temperature. Nitromethane (28.8 mL, 10 equiv.) was added and the reaction was stirred at reflux for 5 hours. The mixture was cooled to room temperature, concentrated, re-dissolved in EtOAc and washed with brine. The organic layer was dried over $Na_2SO_4$, concentrated and purified by column chromatography (20% EtOAc/Hexanes) to provide the desired compound (9.96 g, 62%) as an off-white solid. $^1$H NMR (500 MHz, CDCl$_3$) δ 7.85 (d, J=9.1 Hz, 2H), 7.36-7.24 (m, 5H), 6.63 (d, J=9.2 Hz, 2H), 4.87 (dd, J=12.6, 5.9 Hz, 1H), 4.68 (dd, J=12.6, 8.9 Hz, 1H), 4.24 (tt, J=8.6, 5.9 Hz, 1H), 3.42 (q, J=7.1 Hz, 4H), 3.37 (dd, J=17.0, 6.0 Hz, 1H), 3.29 (dd, J=17.1, 8.2 Hz, 1H), 1.21 (t, J=7.1 Hz, 6H). $^{13}$C NMR (125 MHz, CDCl$_3$) δ 194.57, 151.71, 140.09, 130.90, 129.19, 127.87, 127.78, 123.86, 110.48, 80.03, 44.82, 40.96, 40.00, 12.76.

(Z)—N,N-diethyl-4-(5-((5-(4-methoxyphenyl)-3-phenyl-2H-pyrrol-2-ylidene)amino)-4-phenyl-1Hpyrrol-2-yl)aniline (5)

To a suspension of 42 (1.05 g, 3.08 mmol) in n-BuOH (60 mL) was added 3 (1.85 g, 2 equiv.). The mixture was heated at 70° C. until the solids were completely dissolved. NH$_4$OAc (3.57 g, 15 equiv.) was added, and the mixture was refluxed for 3 hours. The resulting dark green solution was cooled to room temperature, concentrated, dissolved in CH$_2$Cl$_2$ and washed with brine. The organic layer was separated, and the aqueous layer was back extracted with CH$_2$Cl$_2$ (×3). The combined organic layers were dried with Na$_2$SO$_4$ and concentrated. The mixture was purified by column chromatography (20-40% CH$_2$Cl$_2$/Hexanes) to afford the desired product (410 mg, 24%) as a blue-green solid. $^1$H NMR (500 MHz, CDCl$_3$) δ 8.13-8.06 (m, 4H), 7.95 (d, J=9.0 Hz, 2H), 7.78 (d, J=8.8 Hz, 2H), 7.46-7.38 (m, 4H), 7.38-7.33 (m, 1H), 7.33-7.27 (m, 2H), 7.05 (d, J=8.8 Hz, 2H), 6.97 (s, 1H), 6.79 (d, J=9.0 Hz, 2H), 3.91 (s, 3H), 3.49 (q, J=7.1 Hz, 4H), 1.27 (t, J=7.0 Hz, 6H). $^{13}$C NMR (125 MHz, CDCl$_3$) δ 163.38, 160.31, 150.19, 145.97, 144.34, 143.64, 141.90, 136.53, 134.89, 134.06, 129.83, 129.44, 128.98, 128.38, 128.37, 128.18, 127.26, 127.13, 125.16, 119.70, 118.83, 114.85, 111.81, 109.91, 55.71, 44.88, 12.98. HR-MS calcd for $C_{37}H_{35}N_4O^+$[M+H]$^+$ 551.2811, found 551.2800.

Red-HyP-1

To a solution of 5 (53.0 mg, 0.096 mmol) in anhydrous CH$_2$Cl$_2$ (2.0 mL) was added DIPEA (0.168 mL, 10 equiv.) followed by BF$_3$×OEt$_2$ (0.177 mL, 15 equiv.). The reaction was stirred at room temperature for 2 hours, then quenched with the addition of saturated NaHCO$_3$. The organic layer was separated, and the aqueous layer was back extracted with CH$_2$Cl$_2$ (×3). The combined organic layers were dried over Na$_2$SO$_4$ and concentrated. The crude solid was purified by column chromatography (40-50% CH$_2$Cl$_2$/Hexanes) to afford the desired product (48.9 mg, 85%) as a dark pink solid. $^1$H NMR (500 MHz, CDCl$_3$) δ 8.21 (d, J=9.2 Hz, 2H), 8.13-8.02 (m, 6H), 7.52-7.41 (m, 5H), 7.40-7.33 (m, 1H), 7.27 (s, 1H), 7.02 (d, J=8.9 Hz, 2H), 6.92 (s, 1H), 6.75 (d, J=9.3 Hz, 2H), 3.89 (s, 3H), 3.47 (q, J=7.1 Hz, 4H), 1.25 (t, J=7.2 Hz, 6H). $^{13}$C NMR (125 MHz, CDCl$_3$) δ 160.94, 160.17, 152.69, 150.93, 147.18, 143.69, 143.56, 138.80, 133.77, 133.39, 132.61, 131.19, 129.55, 129.43, 129.17, 128.70, 128.64, 128.37, 125.75, 120.16, 117.32, 116.77, 114.18, 111.84, 55.58, 45.00, 12.99. HR-MS calcd for $C_{37}H_{34}BF_2N_4O^+$[M+H]$^+$ 599.2794, found 599.2795.

HyP-1

A solution of red-HyP-1 (71.3 mg, 0.119 mmol) in CH$_2$Cl$_2$ (2.4 mL) was cooled to 0° C. in an ice bath. NaHCO$_3$ (30 mg, 1.1 equiv.) and m-CPBA (77% w/w, 80 mg, 1.1 equiv.) were added, and the mixture was warmed to room temperature and stirred for 2 hours. The mixture was then poured into a solution of saturated NaHCO$_3$ and extracted with EtOAc (×3). The organic layers were combined, and the solvent was removed to yield a dark green film. The crude product was purified by column chromatography to afford the desired product (15 mg, 47%) as a dark green solid. $^1$H NMR (500 MHz, CDCl$_3$) δ 8.08 (dd, J=9.0, 2.7 Hz, 4H), 7.99 (td, J=8.4, 1.6 Hz, 4H), 7.83 (d, J=8.7 Hz, 2H), 7.43-7.31 (m, 6H), 7.06 (s, 1H), 6.96 (d, J=9.0 Hz, 2H), 6.94 (s, 1H), 3.82 (s, 3H), 3.81-3.68 (m, 4H), 1.13 (t, J=7.0 Hz, 6H). $^{13}$C NMR (125 MHz, CDCl$_3$) δ 170.05, 162.85, 161.42, 154.13, 146.74, 145.35, 144.45, 142.15, 132.58, 132.23, 131.87, 130.07, 129.87, 129.46, 129.22, 129.19, 128.67, 128.62, 123.33, 122.03, 119.96, 118.01, 117.98, 114.52, 66.84, 55.55, 29.71. HR-MS calcd for $C_{37}H_{34}BF_2N_4O_2^+$[M+H]$^+$ 615.2737, found 615.2742.

Example 10. Synthesis of rHyP-1 and Red-rHyP-1

Scheme 2 summarizes the imaging probes prepared and characterized. For a full discussion of the results see: Knox, H. J., et al., *ACS Chem Biol.* 2018 Jul. 20; 13(7):1838-1843 and corresponding Supporting Information, incorporated herein by reference.

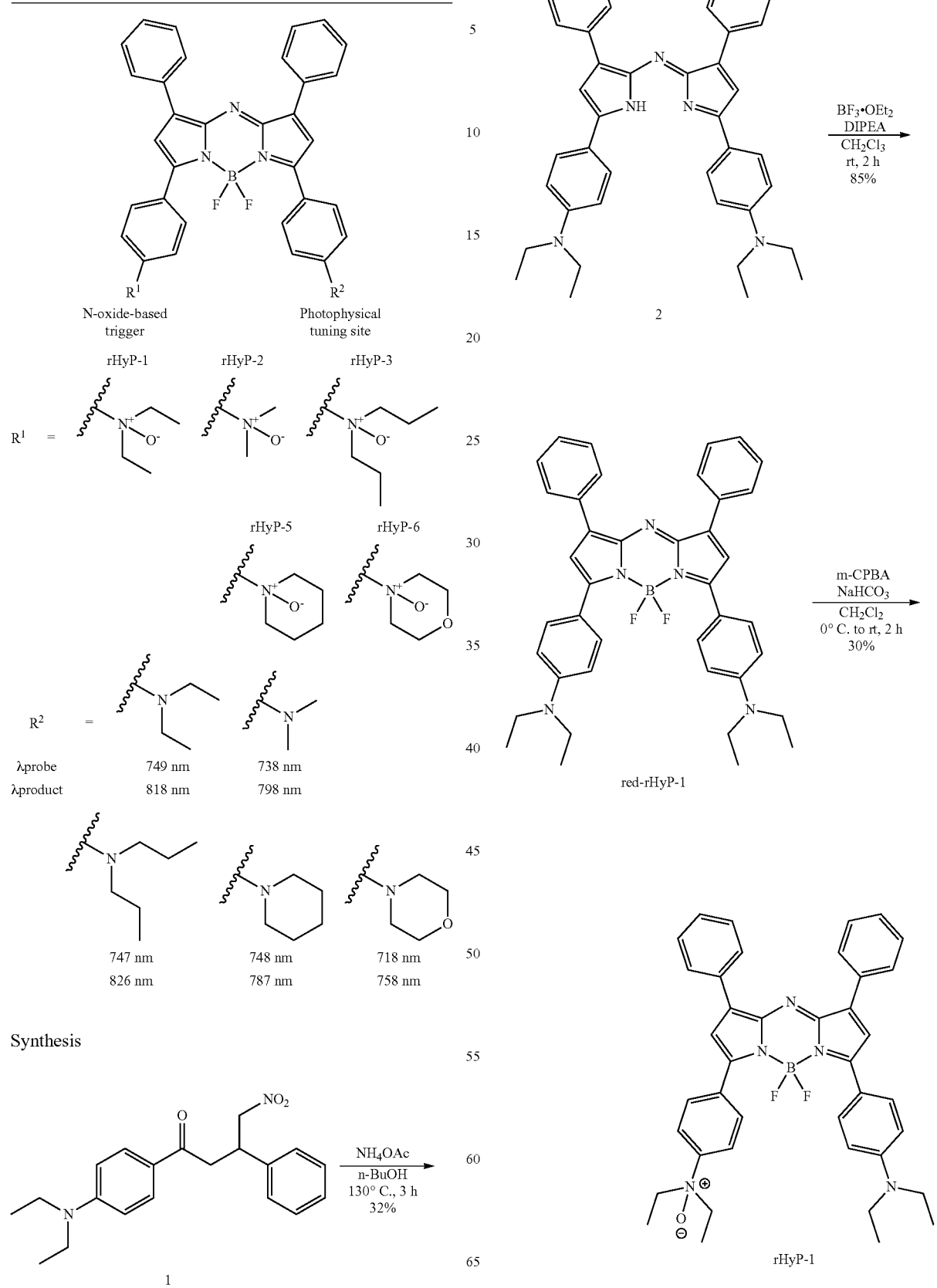

(Z)-4-(2-((5-(4-(diethylamino)phenyl)-3-phenyl-1H-pyrrol-2-yl)imino)-3-phenyl-2H-pyrrol-5-yl)-N,N-diethylaniline (2)

To a suspension of 1 (772 mg, 2.27 mmol) in n-BuOH (22 mL) was added NH₄OAc (2.62 g, 34 mmol, 15 equiv.). The mixture was heated to reflux for 3 hours. The resulting dark green solution was cooled to room temperature, concentrated, dissolved in CH₂Cl₂ and washed with brine. The organic layer was separated and the aqueous layer was back extracted with CH₂Cl₂ (×3). The combined organic layers were dried with Na₂SO₄ and concentrated. The mixture was purified by column chromatography (60% CH₂Cl₂/Hexanes) to afford the desired product (226 mg, 34%) as a green solid. ¹H NMR (500 MHz, CDCl₃) δ 8.10 (d, J=8.4 Hz, 4H), 7.83 (d, J=8.9 Hz, 4H), 7.41 (t, J=7.6 Hz, 4H), 7.31 (t, J=7.3 Hz, 2H), 7.11 (s, 2H), 6.79 (d, J=9.0 Hz, 4H), 3.48 (q, J=7.1 Hz, 8H), 1.26 (t, J=7.1 Hz, 14H). ¹³C NMR (125 MHz, CDCl₃) δ 153.78, 148.89, 140.91, 134.45, 128.96, 128.24, 128.06, 127.30, 119.50, 113.71, 111.74, 44.53, 29.70, 12.73.

Red-rHyP-1

To a solution of 2 (521 mg, 0.88 mmol) in anhydrous CH₂Cl₂ (90 mL) was added DIPEA (1.53 mL, 10 equiv.) followed by BF₃·OEt₂ (1.52 mL, 14 equiv.). The reaction was stirred at room temperature for 3 hours, then quenched with the addition of saturated NaHCO₃. The organic layer was separated and the aqueous layer was back extracted with CH₂Cl₂ (×3). The combined organic layers were dried over Na₂SO₄ and concentrated. The crude solid was purified by column chromatography (60% CH₂Cl₂/Hexanes) to afford the desired product (504 mg, 85%) as a dark red solid. ¹H NMR (500 MHz, CDCl₃) δ 8.14 (d, J=9.1 Hz, 4H), 8.09 (dd, J=8.3, 1.3 Hz, 4H), 7.45 (t, J=7.5 Hz, 4H), 7.37 (t, J=7.3 Hz, 2H), 7.11 (s, 2H), 6.75 (d, J=9.1 Hz, 4H), 3.45 (q, J=7.1 Hz, 8H), 1.23 (t, J=7.1 Hz, 12H). ¹³C NMR (125 MHz, DMSO-d₆) δ 154.30, 149.52, 143.98, 138.75, 132.47, 132.01, 128.69, 128.49, 118.43, 117.02, 111.46, 43.98, 12.67. [M+H]⁺ 640.3423, found 640.3402.

rHyP-1

A solution of red-rHyP-1 (150 mg, 0.225 mmol) in EtOAc (25 mL) was cooled to 0° C. in an ice bath. NaHCO₃ (4.2 mg, 2.2 equiv.) and m-CPBA (77% w/w, 11 mg, 2.2 equiv.) were added and the mixture was warmed to room temperature and stirred for 1 hour. The mixture was then poured into a solution of saturated NaHCO₃ and extracted with EtOAc (×3). The organic layers were combined and the solvent was removed to yield a dark red film. The crude product was purified by column chromatography (10% MeOH/CH₂Cl₂) to afford the desired product (51 mg, 35%) as a dark red solid. ¹H NMR (500 MHz, CDCl₃) δ 8.24 (d, J=8.8 Hz, 2H), 8.14 (d, J=8.4 Hz, 2H), 8.07 (dd, J=13.2, 7.5 Hz, 4H), 7.86 (d, J=8.8 Hz, 2H), 7.49-7.38 (m, 5H), 7.38-7.30 (m, 2H), 6.92 (s, 1H), 6.72 (d, J=9.3 Hz, 2H), 3.73 (q, J=7.0, 6.0 Hz, 4H), 3.42 (q, J=7.1 Hz, 4H), 1.20 (td, J=7.1, 2.4 Hz, 12H). δ ¹³C NMR (125 MHz, CDCl₃) δ 161.73, 151.57, 148.12, 144.55, 142.55, 136.75, 134.00, 133.72, 133.64, 131.87, 129.60, 129.37, 128.78, 128.51, 128.42, 127.96, 121.73, 121.12, 116.38, 116.01, 111.91, 111.34, 66.78, 44.92, 12.74, 8.50. [M+H]⁺ 656.3372, found 656.3349.

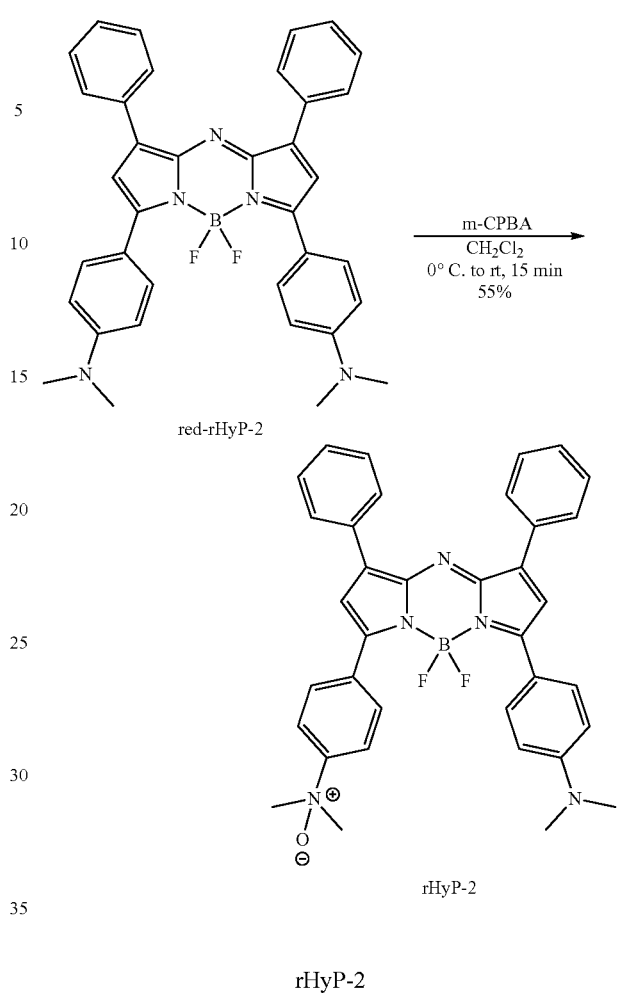

red-rHyP-2 rHyP-2 rHyP-2

A solution of red-rHyP-2 (54.5 mg, 0.093 mmol) in CH₂Cl₂ (1.9 mL) was cooled to 0° C. in an ice bath. NaHCO₃ (8.5 mg, 1.1 equiv.) and m-CPBA (77% w/w, 18.8 mg, 0.9 equiv.) were added and the mixture was warmed to room temperature and stirred for 15 minutes. The mixture was then poured into a solution of saturated NaHCO₃ and extracted with CH₂Cl₂ (×3). The organic layers were combined and the solvent was removed to yield a dark red film. The crude product was purified by column chromatography (7% MeOH/CH₂Cl₂) to afford the desired product (31 mg, 55%) as a dark red solid. ¹H NMR (500 MHz, CDCl₃) 8.20 (d, J=8.8 Hz, 2H), 8.15-8.00 (m, 6H), 7.96 (d, J=7.9 Hz, 2H), 7.49-7.38 (m, 5H), 7.37-7.31 (m, 1H), 7.27 (s, 1H), 6.87 (s, 1H), 6.67 (d, J=8.8 Hz, 2H), 3.64 (s, 6H), 3.02 (s, 6H). ¹³C NMR could not be obtained due to poor solubility. [M+H]⁺ 600.2746, found 600.2751.

(E)-1-(4-fluorophenyl)-3-phenylprop-2-en-1-one (4)

To a solution of 4-fluoroacetophenone 3 (8.76 mL g, 72.4 mmol) in MeOH (160 mL) was added benzaldehyde (7.4 mL, 1 equiv.). Aqueous KOH (10 M, 8.68 mL, 1.2 equiv) was added dropwise and the mixture was stirred for 9 hours. The resulting pale-yellow precipitate was collected by filtration (9.23 g, 56%) and used without further purification. ¹H NMR (500 MHz, CDCl₃) δ 8.07 (dd, J=8.9, 5.4 Hz, 2H), 7.82 (d, J=15.7 Hz, 1H), 7.68-7.62 (m, 2H), 7.51 (d, J=15.6 Hz, 1H), 7.46-7.41 (m, 3H), 7.18 (t, J=8.6 Hz, 2H). ¹³C NMR (125 MHz, CDCl$_3$) δ 188.85, 145.07, 134.77, 134.53, 131.13, 130.66, 129.00, 128.47, 121.61, 115.85, 115.67.

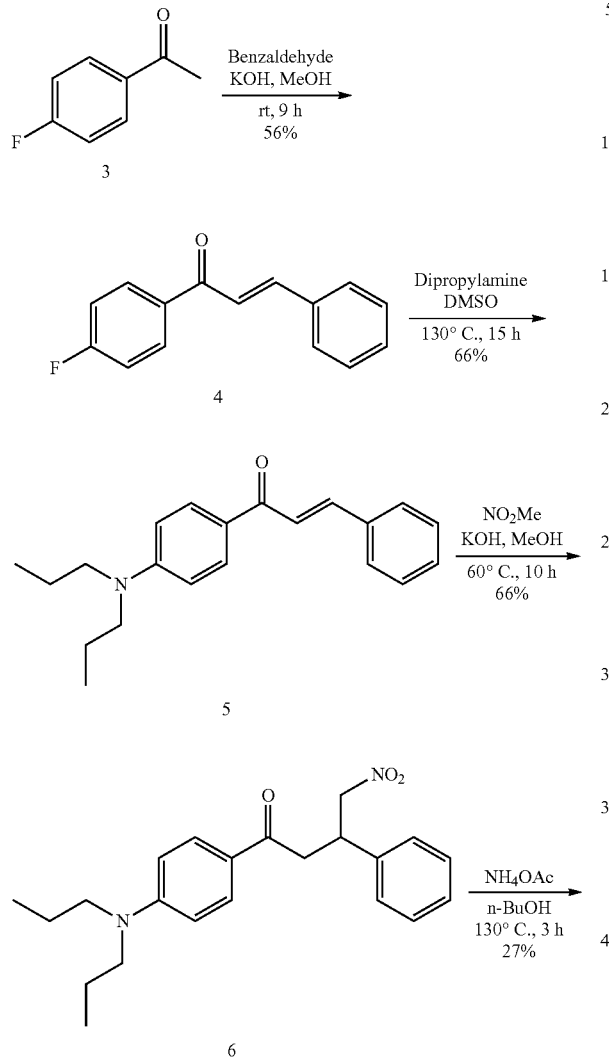

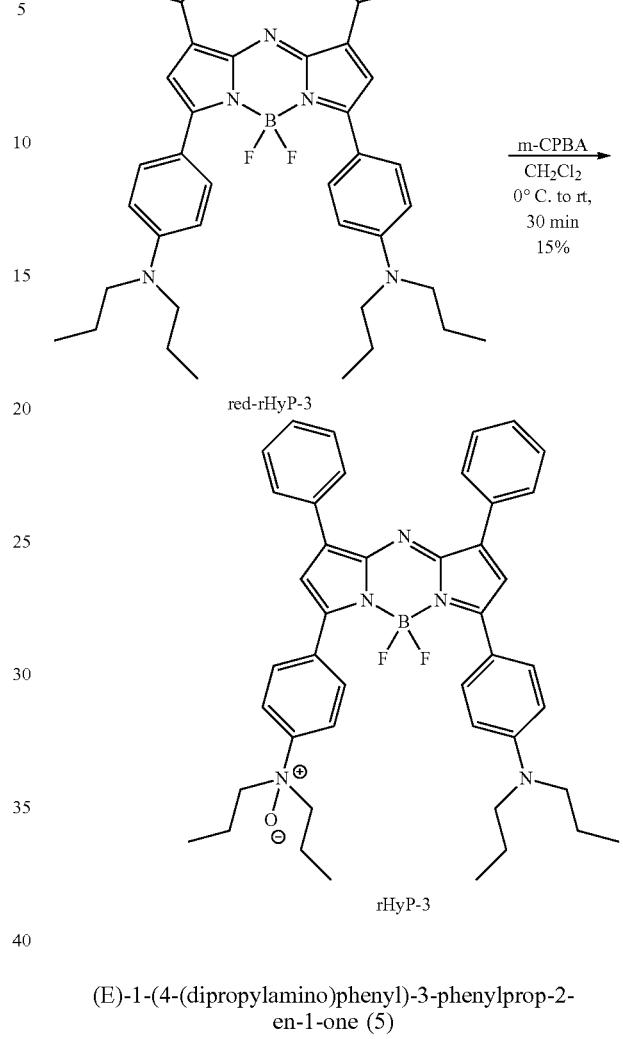

(E)-1-(4-(dipropylamino)phenyl)-3-phenylprop-2-en-1-one (5)

A solution of 4 (2.0 g, 8.84 mmol) and dipropylamine (5.4 mL, 10 equiv.) in DMSO (10 mL) was heated to 130° C. and stirred for 13 hours. The reaction mixture was then cooled to room temperature, concentrated and taken up in CH$_2$Cl$_2$. The solution was washed with brine and the aqueous layer was extracted with CH$_2$Cl$_2$. The organic layer was dried over Na$_2$SO$_4$, concentrated and purified by column chromatography (15% EtOAc/Hexanes) to provide the desired product (1.79 g, 66%) as a yellow oil. $^1$H NMR (500 MHz, CDCl$_3$) δ 7.98 (d, J=9.1 Hz, 2H), 7.78 (d, J=15.6 Hz, 1H), 7.64 (d, J=8.2 Hz, 2H), 7.58 (d, J=15.6 Hz, 1H), 7.40 (qd, J=6.4, 2.8 Hz, 3H), 6.65 (d, J=9.2 Hz, 2H), 3.33 (t, J=7.8 Hz, 4H), 1.66 (q, J=11.1, 7.7 Hz, 4H), 0.96 (t, J=7.3 Hz, 6H). $^{13}$C NMR (125 MHz, CDCl$_3$) δ 187.64, 151.91, 142.48, 135.86, 131.31, 130.06, 129.07, 128.42, 125.50, 122.51, 110.76, 53.05, 20.70, 11.65.

1-(4-(dipropylamino)phenyl)-4-nitro-3-phenylbutan-1-one (6)

To a solution of 5 (810 mg, 2.63 mmol) and nitromethane (1.41 mL, 10 equiv.) in MeOH (15 mL) was added aqueous KOH (10 M, 0.13 mL, 0.5 equiv.). The mixture heated to 60°

C. and stirred for 10 hours. The solution was then cooled to room temperature and concentrated, and the crude product was dissolved in $CH_2Cl_2$ and washed with brine. The organic layer was dried over $Na_2SO_4$ and concentrated. The desired product (260 mg, 27%) was obtained after purification by column chromatography (25% EtOAc/Hexanes). $^1H$ NMR (400 MHz, $CDCl_3$) δ 7.81 (d, J=9.1 Hz, 2H), 7.39-7.23 (m, 5H), 6.58 (d, J=9.1 Hz, 2H), 4.86 (dd, J=12.4, 6.0 Hz, 1H), 4.67 (dd, J=12.6, 8.7 Hz, 1H), 4.22 (td, J=6.0, 2.9 Hz, 1H), 3.39-3.26 (m, 6H), 1.64 (q, J=7.7 Hz, 4H), 0.95 (t, J=7.3 Hz, 6H). $^{13}C$ NMR (125 MHz, $CDCl_3$) δ 194.50, 152.15, 140.00, 130.75, 129.17, 127.85, 127.71, 123.86, 110.61, 79.98, 52.96, 40.93, 39.98, 20.62, 11.58.

(Z)-4-(2-((5-(4-(dipropylamino)phenyl)-3-phenyl-1H-pyrrol-2-yl)imino)-3-phenyl-2H-pyrrol-5-yl)-N,N-dipropylaniline (7)

To a suspension of 6 (215 mg, 0.583 mmol) in n-BuOH (6 mL) was added $NH_4OAc$ (450 mg, 5.83 mmol, 10 equiv.). The mixture was heated to reflux for 4 hours. The resulting dark green solution was cooled to room temperature, concentrated, dissolved in $CH_2Cl_2$ and washed with brine. The organic layer was separated and the aqueous layer was back extracted with $CH_2Cl_2$ (×3). The combined organic layers were dried with $Na_2SO_4$ and concentrated. The mixture was purified by column chromatography (70% $CH_2Cl_2$/Hexanes) to afford the desired product (55.5 mg, 15%) as a green solid. $^1H$ NMR (500 MHz, $CDCl_3$) δ 8.11 (d, J=7.7 Hz, 4H), 7.86-7.79 (m, 4H), 7.42 (t, J=7.3 Hz, 4H), 7.33 (t, J=7.2 Hz, 2H), 7.11 (s, 2H), 6.76 (d, J=8.9 Hz, 4H), 3.35 (t, J=7.7 Hz, 8H), 1.70 (q, J=7.8 Hz, 8H), 0.99 (t, J=7.2 Hz, 12H). $^{13}C$ NMR (125 MHz, $CDCl_3$) δ 153.98, 149.56, 141.11, 134.73, 129.21, 128.43, 128.34, 127.56, 119.62, 113.90, 112.02, 53.14, 20.84, 11.70.

Red-rHyP-3

To a solution of 7 (55.0 mg, 0.085 mmol) in anhydrous $CH_2Cl_2$ (5.0 mL) was added DIPEA (0.148 mL, 10 equiv.) followed by $BF_3 \cdot OEt_2$ (0.134 mL, 15 equiv.). The reaction was stirred at room temperature for 3 hours, then quenched with the addition of saturated $NaHCO_3$. The organic layer was separated and the aqueous layer was back extracted with $CH_2Cl_2$ (×3). The combined organic layers were dried over $Na_2SO_4$ and concentrated. The crude solid was purified by column chromatography (50% $CH_2Cl_2$/Hexanes) to afford the desired product (35.7 mg, 60.5%) as a dark red solid. $^1H$ NMR (500 MHz, $CDCl_3$) δ 8.14 (d, J=8.8 Hz, 4H), 8.10 (d, J=7.2 Hz, 4H), 7.45 (dd, J=8.4, 6.8 Hz, 4H), 7.41-7.35 (m, 2H), 7.11 (s, 2H), 6.72 (d, J=8.7 Hz, 4H), 3.32 (t, J=7.8 Hz, 8H), 1.67 (h, J=7.5 Hz, 8H), 0.96 (t, J=7.4 Hz, 12H). $^{13}C$ NMR (125 MHz, $CDCl_3$) δ 156.07, 150.17, 140.58, 133.49, 132.07, 129.35, 128.60, 118.61, 118.15, 111.75, 109.97, 53.09, 20.91, 11.68. $[M+H]^+$ 696.4049, found 696.4097.

rHyP-3

A solution of red-rHyP-3 (25 mg, 0.035 mmol) in $CH_2Cl_2$ (0.718 mL) was cooled to 0° C. in an ice bath. $NaHCO_3$ (3.3 mg, 1.1 equiv.) and m-CPBA (77% w/w, 8.8 mg, 1.1 equiv.) were added and the mixture was warmed to room temperature and stirred for 30 minutes. The mixture was then poured into a solution of saturated $NaHCO_3$ and extracted with $CH_2Cl_2$ (×3). The organic layers were combined and the solvent was removed to yield a dark red film. The crude product was purified by column chromatography (5% MeOH/$CH_2Cl_2$) to afford the desired product (14 mg, 55%) as a dark red solid. $^1H$ NMR (500 MHz, $CD_2Cl_2$) δ 8.46 (d, J=8.9 Hz, 2H), 8.32 (t, J=8.1 Hz, 4H), 8.25 (d, J=7.6 Hz, 2H), 8.07 (d, J=8.4 Hz, 2H), 7.72-7.61 (m, 5H), 7.55 (d, J=7.1 Hz, 2H), 7.15 (s, 1H), 6.99 (d, J=9.2 Hz, 2H), 3.94-3.70 (m, 4H), 3.62-3.55 (m, 4H), 2.25-2.10 (m, 2H), 1.88 (h, J=7.4 Hz, 4H), 1.60-1.46 (m, 2H), 1.16 (t, J=7.4 Hz, 6H), 1.09 (t, J=7.4 Hz, 6H). $^{13}C$ NMR could not be obtained due to poor solubility. $[M+H]^+$ 712.3998, found 712.3996.

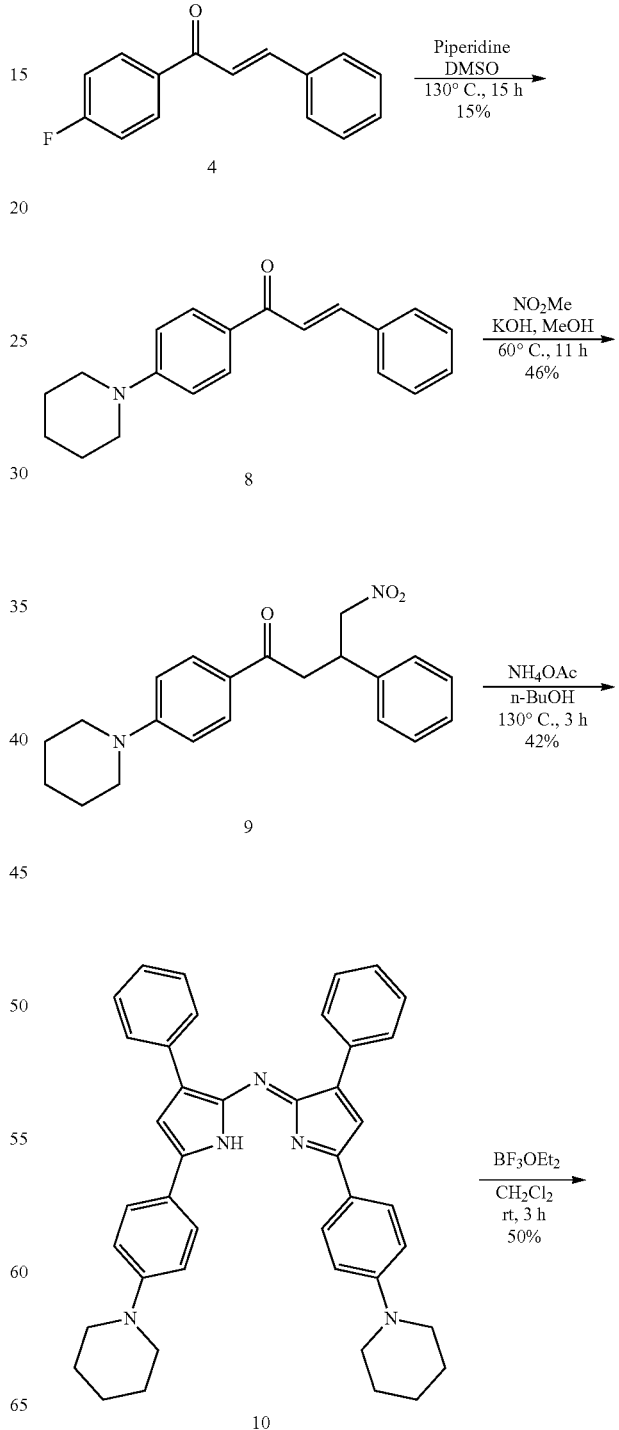

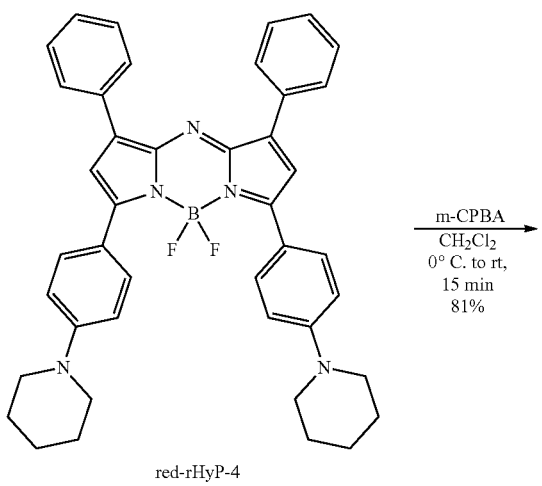

red-rHyP-4

↓ m-CPBA
CH₂Cl₂
0° C. to rt,
15 min
81%

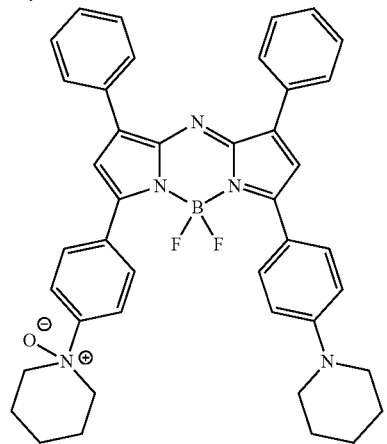

rHyP-4

(E)-3-phenyl-1-(4-(piperidin-1-yl)phenyl)prop-2-en-1-one (8)

A solution of 4 (5.3 g, 23.4 mmol) and piperidine (23.1 mL, 10 equiv.) in DMSO (20 mL) was heated to 130° C. and stirred for 4 hours. The reaction mixture was then cooled to room temperature, concentrated and taken up in CH₂Cl₂. The solution was washed with brine and the aqueous layer was extracted with CH₂Cl₂. The organic layer was dried over Na₂SO₄, concentrated and purified by column chromatography (25% EtOAc/Hexanes) to provide the desired product (1.03 g, 15%) as a yellow solid. $^1$H NMR (500 MHz, CDCl₃) δ 7.99 (d, J=9.0 Hz, 2H), 7.79 (d, J=15.6 Hz, 1H), 7.64 (dd, J=7.6, 1.7 Hz, 2H), 7.56 (d, J=15.6 Hz, 1H), 7.44-7.36 (m, 3H), 6.94 (s, 2H), 3.42-3.38 (m, 4H), 1.72 (s, 6H). $^{13}$C NMR (125 MHz, CDCl₃) δ 187.90, 135.40, 130.77, 130.46, 130.03, 128.86, 128.26, 122.12, 26.09, 25.27, 24.27.

4-nitro-3-phenyl-1-(4-(piperidin-1-yl)phenyl)butan-1-one (9)

To a solution of 8 (1.03 g, 3.54 mmol) and nitromethane (1.90 mL, 10 equiv.) in MeOH (40 mL) was added aqueous KOH (10 M, 0.071 mL, 0.2 equiv.). The mixture heated to 60° C. and stirred for 11 hours. The solution was then cooled to room temperature and concentrated, and the crude product was dissolved in CH₂Cl₂ and washed with brine. The organic layer was dried over Na₂SO₄ and concentrated. The desired product (573 mg, 46%) was obtained after purification by column chromatography (50% EtOAc/Hexanes). $^1$H NMR (500 MHz, CDCl₃) δ 7.85 (d, J=8.8 Hz, 2H), 7.38-7.26 (m, 5H), 6.85 (d, J=8.7 Hz, 2H), 4.88 (dd, J=12.5, 6.1 Hz, 1H), 4.69 (dd, J=12.5, 8.6 Hz, 1H), 4.30-4.19 (m, 1H), 3.45-3.27 (m, 6H), 1.69 (s, 6H). $^{13}$C NMR (125 MHz, CDCl₃) δ 194.63, 154.56, 139.59, 130.28, 128.98, 127.69, 127.46, 125.49, 113.10, 79.70, 48.45, 40.85, 39.63, 25.32, 24.36.

(Z)-3-phenyl-N-(3-phenyl-5-(4-(piperidin-1-yl)phenyl)-1H-pyrrol-2-yl)-5-(4-(piperidin-1-yl)phenyl)-2H-pyrrol-2-imine (10)

To a suspension of 9 (250 mg, 0.709 mmol) in n-BuOH (7 mL) was added NH₄OAc (547 mg, 7.09 mmol, 10 equiv.). The mixture was heated to reflux for 4 hours. The resulting dark green solution was cooled to room temperature, concentrated, dissolved in CH₂Cl₂ and washed with brine. The organic layer was separated and the aqueous layer was back extracted with CH₂Cl₂ (×3). The combined organic layers were dried with Na₂SO₄ and concentrated. The mixture was purified by column chromatography (CH₂Cl₂) to afford the desired product (182 mg, 42%) as a green solid. $^1$H NMR (500 MHz, CDCl₃) 8.08 (d, J=7.4 Hz, 4H), 7.89-7.77 (m, 4H), 7.41 (t, J=7.4 Hz, 4H), 7.32 (t, J=7.1 Hz, 2H), 7.12 (s, 2H), 7.00 (s, 4H), 3.36 (s, 8H), 1.76-1.70 (m, 8H), 1.69-1.64 (m, 4H). $^{13}$C NMR (125 MHz, CDCl₃) δ 153.74, 152.58, 141.26, 134.27, 128.99, 128.12, 127.87, 127.47, 121.94, 115.27, 114.00, 49.32, 29.72, 25.60, 24.38.

Red-rHyP-4

To a solution of 10 (381 mg, 0.619 mmol) in anhydrous CH₂Cl₂ (6.0 mL) was added DIPEA (1.08 mL, 10 equiv.) followed by BF₃.OEt₂ (0.98 mL, 15 equiv.). The reaction was stirred at room temperature for 3 hours, then quenched with the addition of saturated NaHCO₃. The organic layer was separated and the aqueous layer was back extracted with CH₂Cl₂ (×3). The combined organic layers were dried over Na₂SO₄ and concentrated. The crude solid was purified by column chromatography (70% CH₂Cl₂/Hexanes) to afford the desired product (205 mg, 50%) as a dark red solid. $^1$H NMR (500 MHz, CDCl₃) δ 8.13 (d, J=9.1 Hz, 4H), 8.10 (d, J=7.1 Hz, 4H), 7.46 (t, J=7.4 Hz, 4H), 7.43-7.37 (m, 2H), 7.12 (s, 2H), 6.96 (d, J=8.4 Hz, 4H), 3.41 (s, 8H), 1.77-1.63 (m, 12H). $^{13}$C NMR (125 MHz, CDCl₃) δ 156.26, 152.47, 145.38, 141.07, 133.00, 131.66, 129.12, 128.39, 120.54, 118.15, 114.23, 48.74, 29.72, 25.52, 24.37. [M+H]$^+$ 664.3423, found 664.3440.

rHyP-4

A solution of red-rHyP-4 (31.2 mg, 0.047 mmol) in CH₂Cl₂ (0.940 mL) was cooled to 0° C. in an ice bath. NaHCO₃ (4.6 mg, 1.1 equiv.) and m-CPBA (77% w/w, 11.6 mg, 1.1 equiv.) were added and the mixture was warmed to room temperature and stirred for 15 minutes. The mixture was then poured into a solution of saturated NaHCO₃ and extracted with CH₂Cl₂ (×3). The organic layers were combined, and the solvent was removed to yield a dark red film. The crude product was purified by column chromatography (5-20% MeOH/CH₂Cl₂) to afford the desired product (26 mg, 81%) as a dark red solid. $^1$H NMR (500 MHz, Acetone-d₆) δ 8.40 (d, J=9.4 Hz, 2H), 8.25 (d, J=9.7 Hz, 2H), 8.18 (d, J=9.6 Hz, 2H), 8.11 (d, J=9.0 Hz, 2H), 7.78 (s, 1H), 7.54 (t, J=7.3 Hz, 2H), 7.48 (t, J=8.2 Hz, 3H), 7.37 (t, 1H), 7.18-7.11 (m, 3H), 6.91 (d, J=9.4 Hz, 2H), 4.92 (s, 2H), 3.67-3.57 (m, 4H), 3.14 (t, J=2.4 Hz, 1H), 2.78 (d, 4H), 2.11-2.04 (m, 2H), 1.27 (t, J=7.1 Hz, 8H). $^{13}$C NMR could not be obtained due to poor solubility. [M+H]$^+$ 680.3372, found 680.3351.

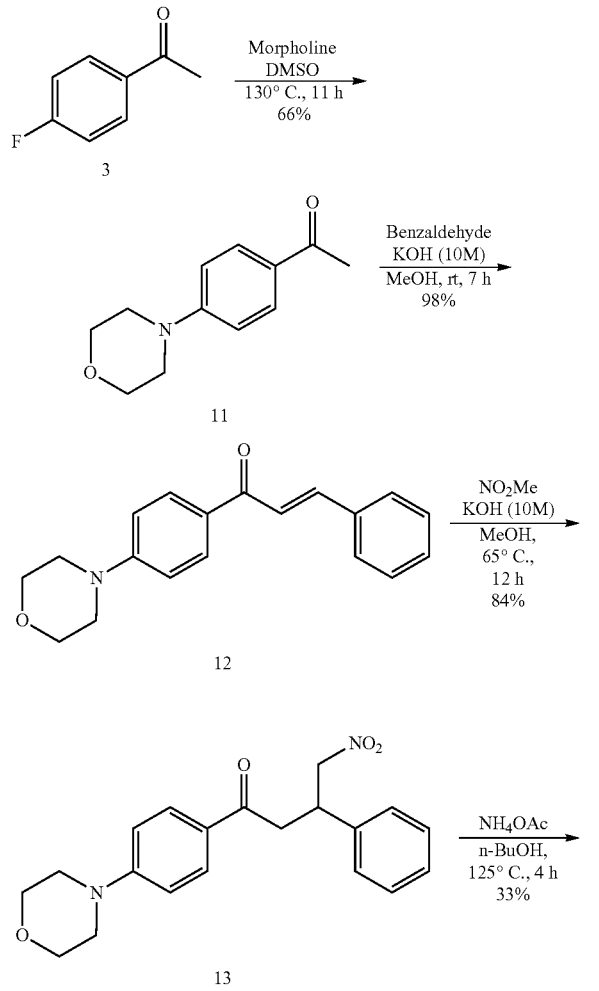

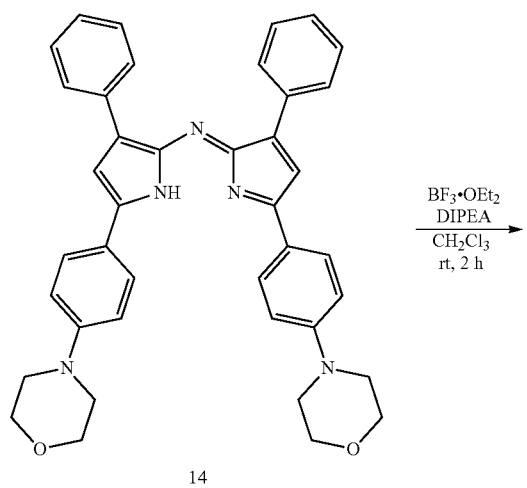

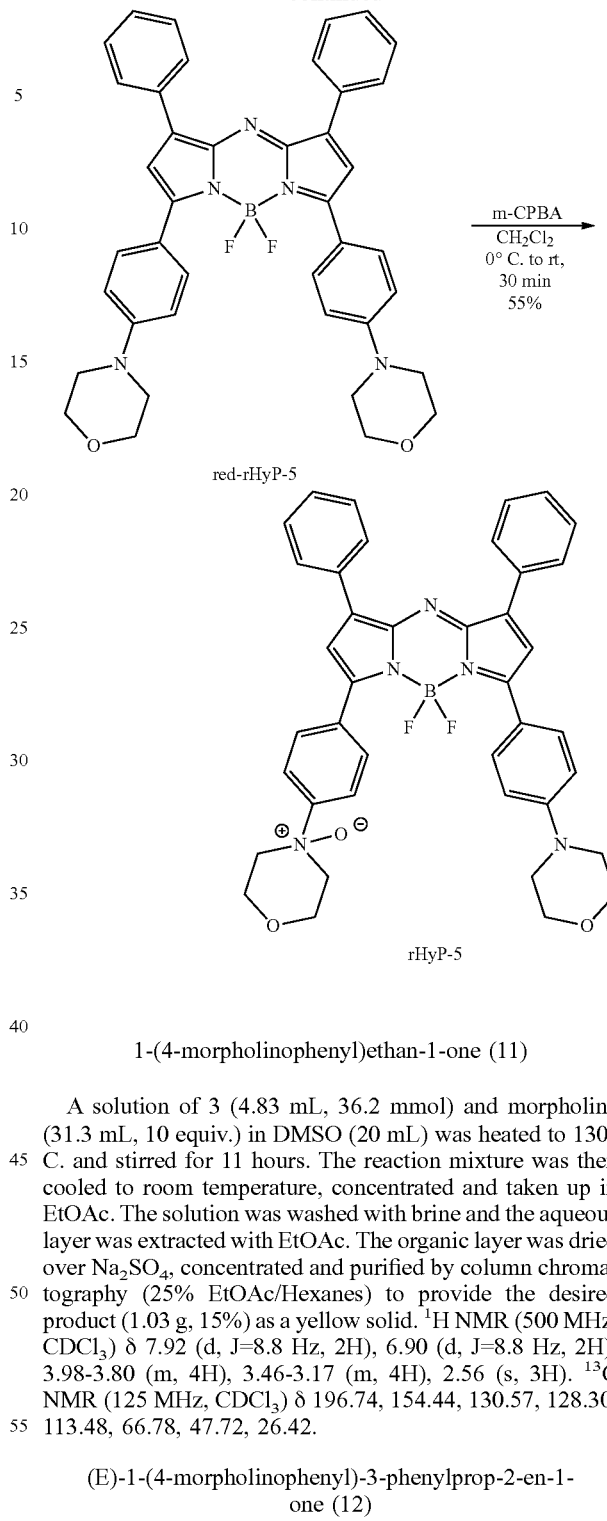

1-(4-morpholinophenyl)ethan-1-one (11)

A solution of 3 (4.83 mL, 36.2 mmol) and morpholine (31.3 mL, 10 equiv.) in DMSO (20 mL) was heated to 130° C. and stirred for 11 hours. The reaction mixture was then cooled to room temperature, concentrated and taken up in EtOAc. The solution was washed with brine and the aqueous layer was extracted with EtOAc. The organic layer was dried over Na$_2$SO$_4$, concentrated and purified by column chromatography (25% EtOAc/Hexanes) to provide the desired product (1.03 g, 15%) as a yellow solid. $^1$H NMR (500 MHz, CDCl$_3$) δ 7.92 (d, J=8.8 Hz, 2H), 6.90 (d, J=8.8 Hz, 2H), 3.98-3.80 (m, 4H), 3.46-3.17 (m, 4H), 2.56 (s, 3H). $^{13}$C NMR (125 MHz, CDCl$_3$) δ 196.74, 154.44, 130.57, 128.30, 113.48, 66.78, 47.72, 26.42.

(E)-1-(4-morpholinophenyl)-3-phenylprop-2-en-1-one (12)

To a solution of 11 (7.43 g, 36.2 mmol) in MeOH (50 mL) was added benzaldehyde (4.1 mL, 1.1 equiv.). Aqueous KOH (10 M, 4.3 mL, 1.2 equiv) was added dropwise and the mixture was stirred for 7 hours at room temperature. The mixture was then concentrated and the crude product was dissolve in EtOAc and washed with brine. The organic layer was dried over Na$_2$SO$_4$ and concentrated to give the desired product (10.5 g, 98%), which was used without further purification. ¹H NMR (500 MHz, CDCl₃) 8.04 (d, J=9.0 Hz, 2H), 7.82 (d, J=15.6 Hz, 1H), 7.67 (dd, J=7.5, 1.9 Hz, 2H), 7.59 (d, J=15.6 Hz, 1H), 7.48-7.39 (m, 3H), 6.95 (d, J=9.0 Hz, 2H), 3.93-3.87 (m, 4H), 3.40-3.35 (m, 4H). 6 ¹³C NMR (125 MHz, CDCl₃) δ 187.61, 151.03, 142.24, 135.62, 131.02, 129.82, 128.82, 128.19, 125.55, 122.33, 110.93, 47.61, 25.47.

1-(4-morpholinophenyl)-4-nitro-3-phenylbutan-1-one (13)

To a solution of 12 (4.68 g, 15.4 mmol) and nitromethane (8.27 mL, 10 equiv.) in MeOH (100 mL) was added aqueous KOH (10 M, 0.310 mL, 0.2 equiv.). The mixture heated to 65° C. and stirred for 24 hours. The solution was then cooled to room temperature and concentrated, and the crude product was dissolved in EtOAc and washed with brine. The organic layer was dried over Na₂SO₄ and concentrated. The desired product (4.56 g, 84%) was obtained after purification by column chromatography (30% EtOAc/Hexanes). ¹H NMR (500 MHz, CDCl₃) δ 7.87 (d, J=9.0 Hz, 2H), 7.41-7.22 (m, 5H), 6.86 (d, J=9.1 Hz, 2H), 4.86 (dd, J=12.5, 6.3 Hz, 1H), 4.69 (dd, J=12.5, 8.4 Hz, 1H), 4.23 (ddd, J=14.3, 8.0, 6.3 Hz, 1H), 3.88-3.85 (m, 4H), 3.44-3.28 (m, 6H). ¹³C NMR (125 MHz, CDCl₃) δ 195.16, 154.69, 139.71, 130.38, 129.25, 127.71, 127.26, 113.45, 79.92, 66.76, 47.56, 41.19, 39.77.

(Z)-5-(4-morpholinophenyl)-N-(5-(4-morpholinophenyl)-3-phenyl-1H-pyrrol-2-yl)-3-phenyl-2H-pyrrol-2-imine (14)

To a suspension of 13 (1.5 g, 4.23 mmol) in n-BuOH (75 mL) was added NH₄OAc (5.0 g, 65 mmol, 15 equiv.). The mixture was heated to reflux for 4 hours. The resulting dark green solution was cooled to room temperature, concentrated, dissolved in CH₂Cl₂ and washed with brine. The organic layer was separated and the aqueous layer was back extracted with CH₂Cl₂ (×3). The combined organic layers were dried with Na₂SO₄ and concentrated. The mixture was purified by column chromatography (1% MeOH/CH₂Cl₂) to afford the desired product (182 mg, 33%) as a green solid. ¹H NMR (500 MHz, CDCl₃) δ 8.07 (d, J=7.7 Hz, 4H), 7.82 (d, J=8.3 Hz, 4H), 7.42 (t, J=7.5 Hz, 4H), 7.34 (t, J=7.3 Hz, 2H), 7.11 (s, 2H), 6.96 (d, J=8.4 Hz, 4H), 3.86 (s, 8H), 3.27 (s, 8H). ¹³C NMR (125 MHz, CDCl₃) δ 154.05, 152.31, 141.77, 134.34, 129.24, 128.41, 128.07, 127.88, 123.44, 115.20, 114.34, 66.93, 48.37.

Red-rHyP-5

To a solution of 14 (783 mg, 1.27 mmol) in anhydrous CH₂Cl₂ (25 mL) was added DIPEA (2.14 mL, 10 equiv.) followed by BF₃.OEt₂ (2.34 mL, 15 equiv.). The reaction was stirred at room temperature for 3 hours, then quenched with the addition of saturated NaHCO₃. The organic layer was separated and the aqueous layer was back extracted with CH₂Cl₂ (×3). The combined organic layers were dried over Na₂SO₄ and concentrated. The crude solid was purified by column chromatography (0.5% MeOH/CH₂Cl₂) to afford the desired product (442 mg, 52%) as a dark red solid. ¹H NMR (500 MHz, CDCl₃) δ 8.14 (d, J=9.1, 4H), 8.09 (d, J=9.55 4H), 7.47 (t, J=8.1 Hz, 4H), 7.45-7.38 (m, 2H), 7.10 (s, 2H), 6.98 (d, J=8.7 Hz, 4H), 3.89 (t, J=4.9 Hz, 8H), 3.37 (t, J=4.9 Hz, 8H). ¹³C NMR (125 MHz, CDCl₃) δ 157.11, 152.62, 145.52, 142.11, 133.02, 131.74, 129.43, 129.12, 128.71, 122.12, 118.59, 114.24, 66.87, 47.74. [M+H]⁺ 668.5758, found 668.3026.

rHyP-5

A solution of red-rHyP-5 (72 mg, 0.108 mmol) in CH₂Cl₂ (0.940 mL) was cooled to 0° C. in an ice bath. NaHCO₃ (10 mg, 1.1 equiv.) and m-CPBA (77% w/w, 20 mg, 1.1 equiv.) were added and the mixture was warmed to room temperature and stirred for 30 minutes. The mixture was then poured into a solution of saturated NaHCO₃ and extracted with CH₂Cl₂ (×3). The organic layers were combined, and the solvent was removed to yield a dark red film. The crude product was purified by column chromatography (6% MeOH/CH₂Cl₂) to afford the desired product (41 mg, 55%) as a dark red solid. ¹H NMR (500 MHz, CDCl₃) δ 8.20 (d, J=9.2 Hz, 2H), 8.16 (d, J=9.0 Hz, 2H), 8.12-8.06 (m, 4H), 8.05 (d, J=7.2 Hz, 2H), 7.51-7.42 (m, 5H), 7.41-7.35 (m, 1H), 7.25 (s, 1H), 6.93 (d, J=9.0 Hz, 3H), 4.76 (t, J=12.0 Hz, 2H), 4.05-3.90 (m, 4H), 3.84 (d, J=4.8 Hz, 4H), 3.39 (d, J=5.0 Hz, 4H), 3.37-3.31 (m, 2H). ¹³C NMR (125 MHz, CDCl₃) δ 161.80, 154.19, 153.44, 150.81, 147.57, 145.26, 143.43, 134.04, 133.05, 132.88, 131.79, 130.30, 129.83, 129.44, 129.00, 128.64, 128.61, 128.55, 120.39, 119.74, 116.98, 113.56, 67.42, 66.43, 62.27, 46.89. [M+H]⁺ 684.2958, found 684.2496.

TABLE 2

Photophysical properties of rHyP compounds and their reduced products (Red-rHyP).

| Compound | ε (M⁻¹·cm¹) | λ$_{abs}$ (nm) | Φ | cLogP |
|---|---|---|---|---|
| rHyP-1 | 5.8 × 10⁴ | 749 | 0.013 | 10.36 |
| red-rHyP-1 | 9.9 × 10⁴ | 818 | 0.013 | 11.29 |
| rHyP-2 | 4.6 × 10⁴ | 738 | 0.021 | 8.94 |
| red-rHyP-2 | 8.2 × 10⁴ | 798 | 0.023 | 9.17 |
| rHyP-3 | 8.0 × 10⁴ | 747 | 0.013 | 12.48 |
| red-rHyP-3 | 9.3 × 10⁴ | 826 | 0.010 | 13.4 |
| rHyP-4 | 9.1 × 10⁴ | 748 | 0.011 | 10.81 |
| red-rHyP-4 | 7.6 × 10⁴ | 787 | 0.017 | 10.52 |
| rHyP-5 | 9.2 × 10⁴ | 718 | 0.049 | 7.95 |
| red-rHyP-5 | 7.6 × 10⁴ | 758 | 0.085 | 7.75 |
| HyP-1 | 1.5 × 10⁴ | 670 | 0.33 | 9.06 |
| red-HyP-1 | 5.4 × 10⁴ | 760 | 0.11 | 9.98 |

Example 11. Synthesis of HyP-650 and Red-HyP-650

Synthesis of HyP-650 compounds is shown below. Table 3 summarizes the photophysical characterization of HyP-650 compounds. For a full discussion of the results see: Chen, M., et al., Optics Letters Vol. 44, Issue 15, pp. 3773-3776 (2019) and corresponding Supporting Information, incorporated herein by reference.

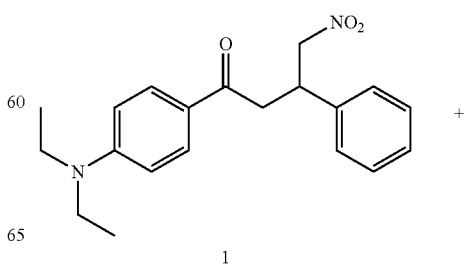

1

-continued

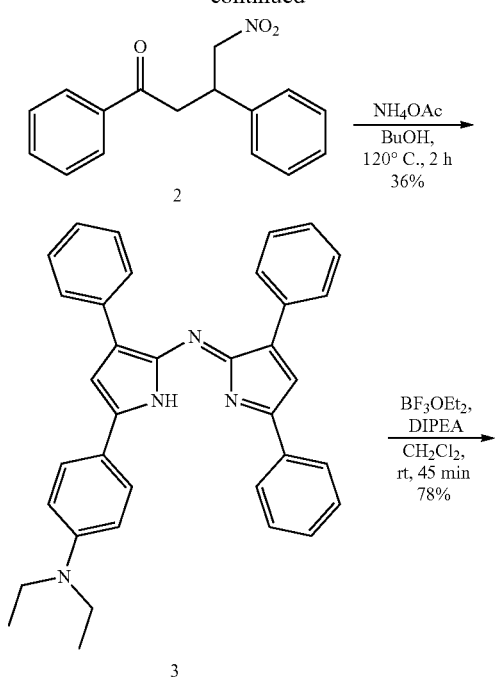

2

NH₄OAc
BuOH,
120° C., 2 h
36%

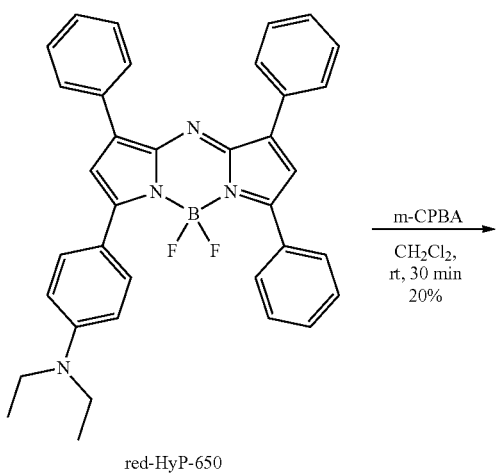

3

BF₃OEt₂,
DIPEA
CH₂Cl₂,
rt, 45 min
78% red-HyP-650 m-CPBA
CH₂Cl₂,
rt, 30 min
20%

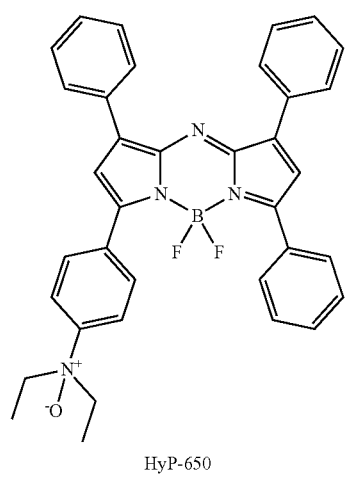

HyP-650

(Z)-4-(5-((3,5-diphenyl-2H-pyrrol-2-ylidene)amino)-4-phenyl-1H-pyrrol-2-yl)-N,N-diethylaniline (3)

1 (689 mg, 2.02 mmol) and 2 (454 mg, 1.69 mmol) were combined in n-butanol (30 mL). The mixture was heated to 70° C. until all solids were fully dissolved, then NH₄OAc (1.95 g, 15 equiv.) was added and solution was heated to 110° C. for 2 hours. The resulting blue-green solution was cooled to room temperature and concentrated. The solid was dissolved in CH₂Cl₂ and washed with brine. The organic layer was removed, and the aqueous layer was extracted with CH₂Cl₂ (×3). The combined organic layers were dried over Na₂SO₄ and concentrated, and the crude solid was purified by column chromatography (40% CH₂Cl₂/Hexanes) to afford the final product (313 mg, 36%) as a blue-green solid. $^1$H NMR (500 MHz, CDCl₃) δ 7.99 (d, J=7.0 Hz, 4H), 7.90 (d, J=9.0 Hz, 2H), 7.68 (d, J=7.0 Hz, 2H), 7.40 (t, J=7.8 Hz, 2H), 7.35-7.23 (m, 7H), 7.20 (t, J=7.4 Hz, 1H), 7.16 (s, 1H), 6.89 (s, 1H), 6.67 (d, J=9.0 Hz, 2H), 3.38 (q, J=7.1 Hz, 4H), 1.16 (t, J=7.1 Hz, 6H). 13C NMR (125 MHz, CDCl3) δ 167.75, 159.45, 150.59, 147.88, 141.13, 139.81, 134.90, 133.99, 133.69, 131.97, 130.40, 129.41, 128.76, 128.32, 128.29, 128.27, 128.03, 126.98, 125.09, 121.12, 119.77, 111.68, 108.61, 44.82, 12.86.

4-(5,5-difluoro-1,7,9-triphenyl-5H-5⁴,6⁴-dipyrrolo[1,2-c:2',1'-f][1,3,5,2]triazaborinin-3-yl)-N,N-diethylaniline (red-HyP-650)

3 (313 mg, 0.60 mmol) was dissolved in anhydrous CH₂Cl₂ (10 mL). DIPEA (1.05 mL, 10 equiv.) was added via syringe, followed by BF₃OEt₂ (1.11 mL, 15 equiv.). The solution was stirred under a nitrogen atmosphere for 45 minutes, during which time the color changed from dark blue to dark red. The reaction mixture was quenched via addition of saturated NaHCO₃. The organic layer was separated, and the aqueous layer was extracted with CH₂Cl₂ (×3). The combined organic layers were dried over Na₂SO₄ and concentrated. The crude solid was purified by column chromatography (40-80% CH₂Cl₂/Hexanes) to yield the desired product (267 mg, 78%) as a dark red solid. $^1$H NMR (500 MHz, DMF-d₇) δ 8.53 (d, J=9.1 Hz, 2H), 8.34 (d, J=7.1 Hz, 2H), 8.24 (d, J=7.6 Hz, 2H), 8.14 (s, 1H), 8.12 (d, J=7.3 Hz, 2H), 7.63-7.39 (m, 9H), 7.26 (s, 1H), 7.00 (d, J=9.5 Hz, 1H), 3.67 (q, J=7.1 Hz, 4H), 1.26 (t, J=7.1 Hz, 6H). $^{19}$F NMR (471 MHz, DMF-d₇) 6-132.08 (dd, J=65.6, 32.5 Hz).

4-(5,5-difluoro-1,7,9-triphenyl-5H-5⁴,6⁴-dipyrrolo[1,2-c:2',1'-f][1,3,5,2]triazaborinin-3-yl)-N,N-diethylaniline oxide (HyP-650)

Red-HyP-650 (43.4 mg, 0.076 mmol) was dissolved in CH₂Cl₂ (1 mL) and the solution was cooled to 0° C. in an ice bath. m-CPBA (14.5 mg, 1.1 equiv) was added, and the mixture was allowed to warm to room temperature. The solution was stirred at room temperature for 30 minutes, during which time the color changed from dark red to royal blue. The reaction mixture was washed with saturated NaHCO₃, the organic layer was removed, and the aqueous layer was extracted with CH₂Cl₂ (×3). The solution was dried over Na₂SO₄ and concentrated. The crude solid was purified by column chromatography (10% MeOH/CH₂Cl₂) to afford the desired product (8 mg, 20%) as a royal blue solid. $^1$H NMR (500 MHz, CDCl₃) δ 8.18 (d, J=8.6 Hz, 2H), 8.12-8.04 (m, 6H), 7.86 (d, J=8.5 Hz, 2H), 7.55-7.42 (m, 9H), 7.09 (s, 1H), 7.06 (s, 1H), 4.15-3.98 (m, 2H), 3.90-3.77

(m, 2H), 1.19 (t, J=7.0 Hz, 6H). $^{19}$F NMR (471 MHz, CDCl$_3$) δ −131.35 (dd, J=62.6, 31.1 Hz).

TABLE 3

Photophysical characterization for HyP-650 and Red-Hyp-650.

| Compound | ε (M$^{-1}$·cm$^1$) | λ$_{abs}$ (nm) | Φ$^a$ |
|---|---|---|---|
| HyP-650 | 4.0 × 10$^4$ | 650 | 0.027 |
| red-HyP-650 | 8.1 × 10$^4$ | 740 | 0.069 |

Data were collected in CHCl3.
$^a$Fluorescence quantum yield.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound comprising:
    a) a bidentate structure having two or more aromatic conjugated groups and two binding heteroatoms;
    b) a bridging moiety bonded to the binding heteroatoms of the bidentate structure;
    c) an optional electron donating substituent conjugated to one group of the two or more conjugated groups; and
    d) a redox moiety conjugated to a second group of the two or more conjugated groups;
    wherein the redox moiety comprises an N-oxide and is a substrate for redox reactions; and
    wherein the compound absorbs electromagnetic radiation at about the near infrared (NIR) region of the electromagnetic spectrum.

2. The compound of claim 1 wherein the compound comprises the electron donating substituent, the electron donating substituent is an alkoxy substituent, and the oxygen atom of the alkoxy substituent is conjugated to one group of the two or more conjugated groups.

3. The compound of claim 1 wherein the bridging moiety comprises an electron deficient atom.

4. The compound of claim 1 wherein the bridging moiety comprises boron.

5. The compound of claim 1 wherein the bidentate structure comprises a tetraarylazadipyrromethene.

6. The compound of claim 1 wherein the compound absorbs electromagnetic radiation at a wavelength of about 600 nm to about 1000 nm.

7. A compound represented by Formula I:

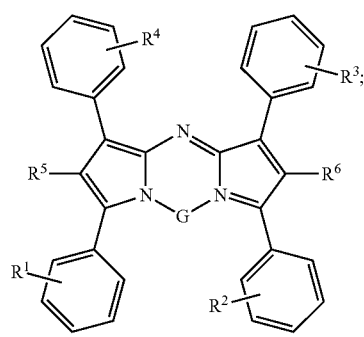

(I)

wherein
    G comprises a metalloid;
    R$^1$ is N(L)(R$^d$)$_2$;
    L is O$^-$;
    each R$^d$ is independently H, —(C$_1$-C$_6$)alkyl, or —(C$_3$-C$_6$)cycloalkyl, or both R$^d$ taken together form a heterocycle with the nitrogen atom of R$^1$;
    R$^2$ is H, halo, —(C$_1$-C$_6$)alkyl, —(C$_3$-C$_6$)cycloalkyl, —OR$^a$, —SR$^b$, or —N(Z)(R$^e$)$_2$ wherein Z is a lone pair;
    each R$^e$ is independently H, —(C$_3$-C$_6$)cycloalkyl or both R$^e$ taken together form a heterocycle;
    R$^3$, R$^4$, R$^5$ and R$^6$ are independently H, halo, —(C$_1$-C$_6$)alkyl, —(C$_3$-C$_6$)cycloalkyl, —OR$^a$, —SR$^b$, or —N(J)(R$^c$)$_2$ wherein J is a lone pair;
    each R$^a$ and R$^b$ are independently H, —(C$_1$-C$_6$)alkyl, or —(C$_3$-C$_6$)cycloalkyl; and
    each R$^c$ is independently H, —(C$_1$-C$_6$)alkyl, or —(C$_3$-C$_6$)cycloalkyl.

8. The compound of claim 7 wherein G is BX$_2$ wherein X is fluoro, chloro, bromo, or iodo.

9. The compound of claim 7 wherein R$^2$ is H, halo, —(C$_1$-C$_6$)alkyl, —(C$_3$-C$_6$)cycloalkyl, —OR$^a$, or —SR$^b$.

10. The compound of claim 7 wherein the compound of Formula I is a compound of Formula II:

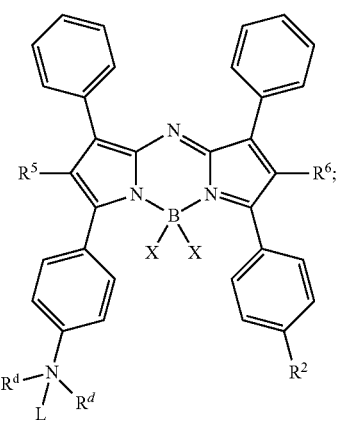

(II)

wherein
    X is halo;
    R$^a$ and R$^b$ are independently —(C$_1$-C$_6$)alkyl or —(C$_3$-C$_6$)cycloalkyl;

each $R^d$ is independently —$(C_1$-$C_6)$alkyl or —$(C_3$-$C_6)$ cycloalkyl, or both $R^d$ taken together form a heterocycle with the nitrogen atom;

each $R^e$ is independently —$(C_1$-$C_6)$alkyl, or —$(C_3$-$C_6)$ cycloalkyl, or both $R^e$ taken together form a heterocycle.

11. The compound of claim 1 wherein the compound of Formula II is:

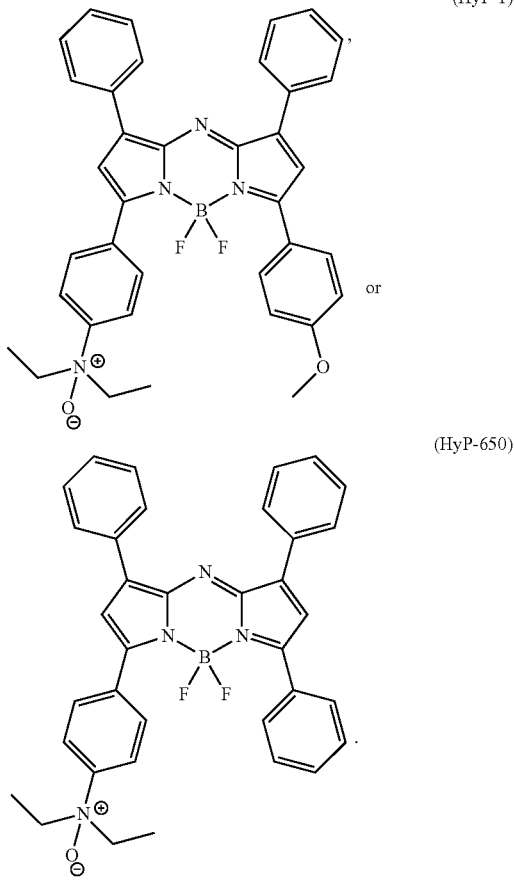

12. A method for fluorescence detection of hypoxia comprising:
a) contacting test cells and the compound of claim 7, wherein the compound is an oxidized compound having an oxidized redox moiety, wherein the oxidized compound and test cells form a test sample;
b) contacting control cells with the oxidized compound, wherein the oxidized compound and the control cells form a control sample;
c) allowing an interval of time to elapse wherein the oxidized redox moiety of the oxidized compound is irreversibly reduced by endogenous reducing agents to form a reduced compound in the test sample when the test cells are deprived of oxygen;
d) irradiating the test sample and control sample with NIR radiation causing the test sample and control sample to emit a fluorescent signal;
e) determining the ratiometric intensity of the fluorescent signal of the test sample and control sample; and
f) detecting the presence of hypoxia in the test sample when the fluorescent signal of the test sample has an intensity greater than the fluorescent signal of the control sample; or detecting the absence of hypoxia in the test sample when the fluorescent signal of the test sample has an intensity about the same as the fluorescent signal of the control sample;
wherein the fluorescent signal of the reduced compound is red shifted by a wavelength of about 50 nm to about 200 nm relative to the compound of claim 7 when hypoxia is present.

13. A method for photoacoustic detection of hypoxia comprising:
a) contacting tissue and the compound of claim 7 in-vivo, wherein the compound is an oxidized compound having an oxidized redox moiety, wherein the oxidized compound and tissue form a sample;
b) allowing an interval of time to elapse wherein the oxidized redox moiety of the oxidized compound is irreversibly reduced by endogenous reducing agents to form a reduced compound in the test sample when the tissue is deprived of oxygen;
c) irradiating the sample with NIR radiation; and
d) detecting a photoacoustic signal from the sample wherein the reduced compound emits a photoacoustic signal;
thereby detecting the presence of hypoxia when present in the sample.

14. The compound Red-HyP-1:

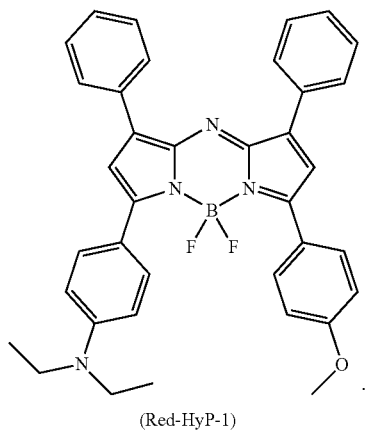

(Red-HyP-1)

15. The compound of claim 1 wherein the compound is not:

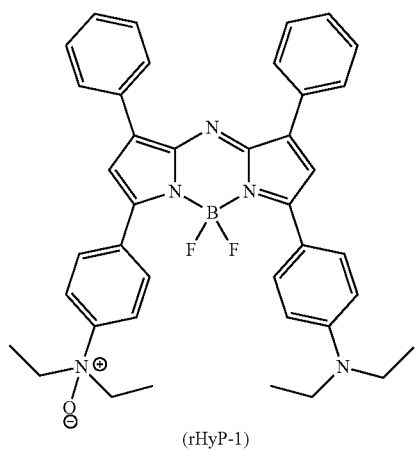

(rHyP-1)

16. The method of claim 13 wherein the reduced compound is fluorescent when irradiated at NIR, wherein fluorescence of the reduced compound is red shifted by about 50 nm to about 200 nm relative to a corresponding oxidized compound.

17. The method of claim 16 wherein the reduced compound emits a photoacoustic signal when irradiated at NIR.

* * * * *